(12) United States Patent
Cheung

(10) Patent No.: US 10,327,671 B2
(45) Date of Patent: Jun. 25, 2019

(54) ALGORITHMS FOR GAIT MEASUREMENT WITH 3-AXES ACCELEROMETER/GYRO IN MOBILE DEVICES

(71) Applicant: Hong Kong Baptist University, Hong Kong (HK)

(72) Inventor: Jeffrey Tai Kin Cheung, Hong Kong (HK)

(73) Assignee: HONG KONG BAPTIST UNIVERSITY, Hong Kong (HK)

(*) Notice: Subject to any disclaimer, the term of this patent is extended or adjusted under 35 U.S.C. 154(b) by 65 days.

(21) Appl. No.: 15/276,798

(22) Filed: Sep. 27, 2016

(65) Prior Publication Data

US 2017/0042453 A1     Feb. 16, 2017

Related U.S. Application Data

(63) Continuation-in-part of application No. 14/622,933, filed on Feb. 16, 2015.

(60) Provisional application No. 61/940,801, filed on Feb. 17, 2014.

(51) Int. Cl.
*A61B 5/11* (2006.01)
*A61B 5/00* (2006.01)
*A61B 5/117* (2016.01)

(52) U.S. Cl.
CPC ............ *A61B 5/112* (2013.01); *A61B 5/1101* (2013.01); *A61B 5/117* (2013.01); *A61B 5/1123* (2013.01); *A61B 5/4082* (2013.01); *A61B 5/6823* (2013.01); *A61B 5/6831* (2013.01); *A61B 5/6898* (2013.01); *A61B 5/7278* (2013.01); *A61B 2503/40* (2013.01); *A61B 2562/0219* (2013.01)

(58) Field of Classification Search
CPC ..... A61B 5/112; A61B 5/7278; A61B 5/6823; A61B 5/1101; A61B 5/4082; A61B 5/117; A61B 5/6898; A61B 5/6831; A61B 2562/0219; A61B 2503/40; A61B 5/1123; A61B 5/0002; A61B 5/1038; A61B 5/1118; A61B 5/4866; A61B 5/6807; A43B 3/0005; A43B 7/00
See application file for complete search history.

(56) References Cited

U.S. PATENT DOCUMENTS 6,571,193 B1 *  5/2003  Unuma ................ A43B 3/0005
                                                    340/853.2
2004/0116836 A1 *  6/2004  Kawai .................. B62D 57/032
                                                    600/595
(Continued)

OTHER PUBLICATIONS

Alessandra Ferreira Barbosa et al., "Gait, posture and cognition in Parkinson's disease", Dec. 2016, Dement Neuropsychol, 10(4), pp. 280-286.*

(Continued)

*Primary Examiner* — Mischita L Henson
(74) *Attorney, Agent, or Firm* — Shun Yao; Park, Vaughan, Fleming & Dowler LLP

(57) ABSTRACT

The present invention relates to a method of gait measurement using tri-axial accelerometer/gyro in mobile devices. In particular, the present invention relates to algorithms for gait measurement using tri-axial accelerometer/gyro in mobile devices for monitoring and improving the physical movement of a moving subject.

16 Claims, 43 Drawing Sheets

(56) References Cited

U.S. PATENT DOCUMENTS

| | | | | |
|---|---|---|---|---|
| 2011/0054359 A1* | 3/2011 | Sazonov | .............. | A43B 3/0005 |
| | | | | 600/595 |
| 2011/0077904 A1* | 3/2011 | Jung | .................... | A43B 3/0005 |
| | | | | 702/152 |
| 2014/0058254 A1* | 2/2014 | Yamaji | .................... | A61B 5/024 |
| | | | | 600/430 |
| 2015/0316579 A1* | 11/2015 | Pakzad | .................... | G01P 15/02 |
| | | | | 702/150 |

OTHER PUBLICATIONS

Philippe Terrier et al., "To What Extent Does Not Wearing Shoes Affect the Local Dynamic Stability of Walking? Effect Size and Intrasession Repeatability".*

Alvaro Muro-de-la-Herran et al., Gait Analysis Methods: An Overview of Wearable and Non-Wearable Systems, Highlighting Clinical Applications, 2014, Sensors, 14, doi:10.3390/s140203362, pp. 3362-3394.*

* cited by examiner

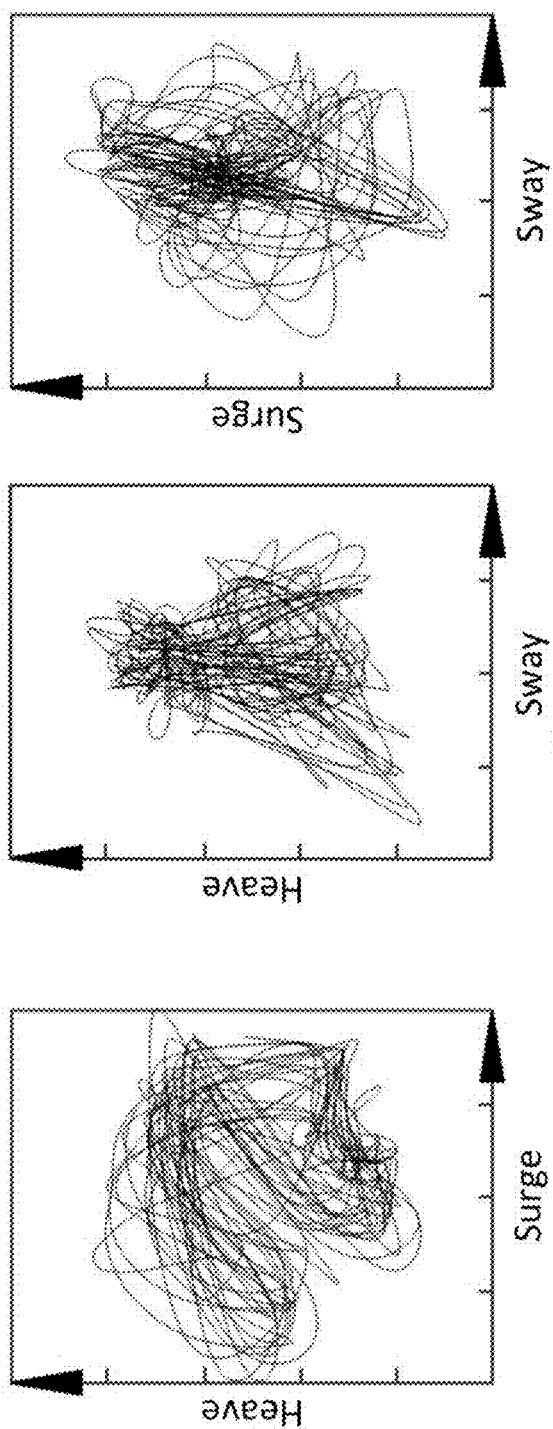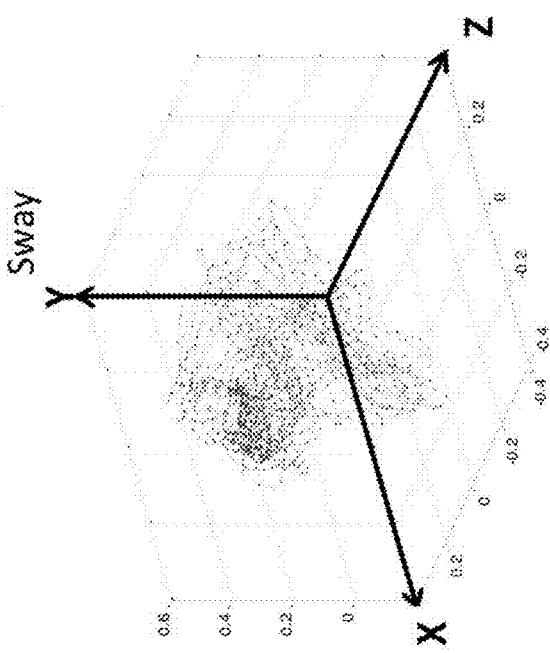
Figure 7c

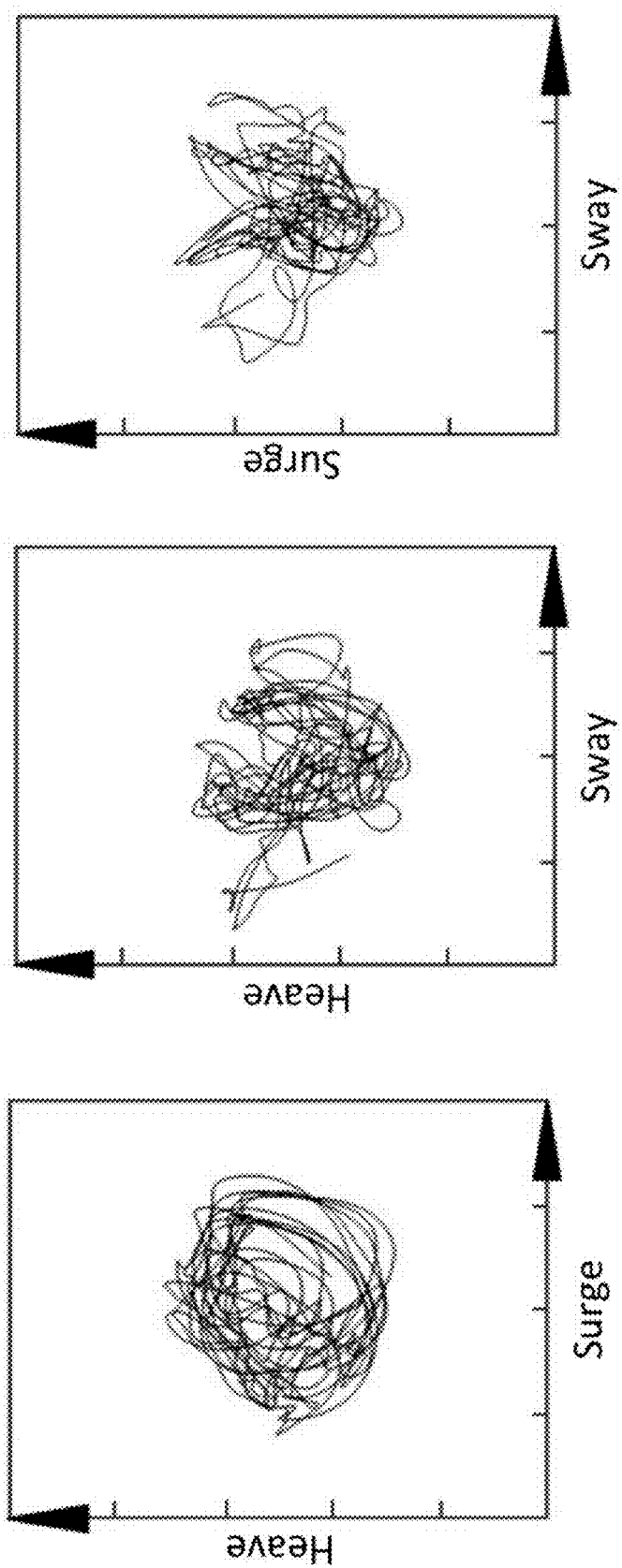

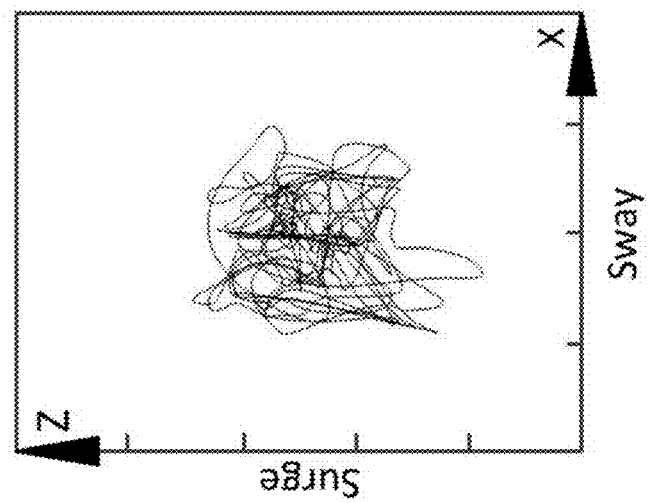
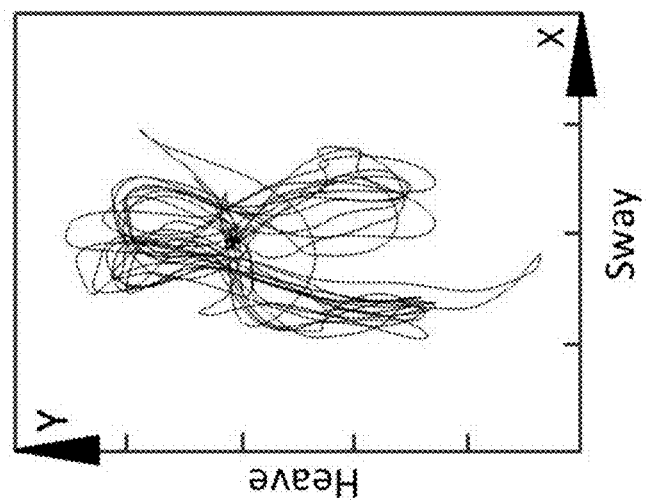
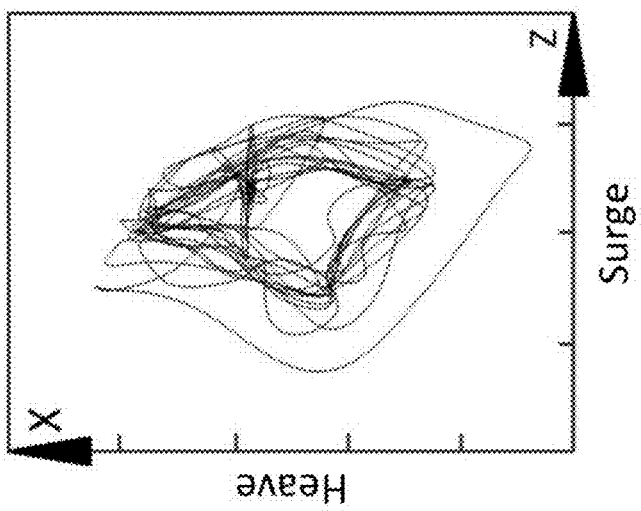
Figure 11b

ALGORITHMS FOR GAIT MEASUREMENT WITH 3-AXES ACCELEROMETER/GYRO IN MOBILE DEVICES

CROSS-REFERENCE TO RELATED APPLICATIONS

This application is a continuation-in-part of U.S. Non-Provisional patent application Ser. No. 14/622,933 filed on Feb. 16, 2015, which claims the benefit of U.S. Provisional Patent Application Ser. No. 61/940,801 filed on Feb. 17, 2014. The disclosures of both U.S. Non-Provisional patent application Ser. No. 14/622,933 and U.S. Provisional Patent Application Ser. No. 61/940,801 are hereby incorporated by reference in their entirety.

FIELD OF THE INVENTION

The present invention relates to a method of gait measurement using tri-axial accelerometer/gyro in mobile devices. In particular, the present invention relates to algorithms for gait measurement using tri-axial accelerometer/gyro in mobile devices for monitoring and improving the physical movement of a moving subject.

BACKGROUND OF THE INVENTION

Gait analysis (the study of walking and running forms) is the key to the study of biomechanics. It is used to monitor and improve body coordination and movement as well as for biometric identification. Traditional gait analysis uses an elaborate optoelectronic setup with multiple Light Emitting Diodes (LEDs) and reflective markers placed on various parts of the subject's body. High-speed cameras are used to capture sequential frames. Due to the cumbersome setup, data are not transmitted wirelessly and the measurement must be conducted in a controlled laboratory environment that not only limits more realistic scenario but also may have an effect on having the subject performing physical movements in a less than natural stance. Useful information is extracted with frame by frame analysis followed by complex algorithms only after the measurement is completed. It is an objective of the present invention to provide a simple gait measurement device coupled with a simple data analysis algorithm. The measurement is not confined to environment with the elaborate setting. It can be carried out under any circumstance and for all types of physical activities. The analysis can be made in a matter of a few seconds to reveal both graphic presentation of gait and postural form in all three motion axes as well as quantitative data known as Dynamic Instability Index (DII) that is a measure of power level exerted by the subject to keep balance while moving. The combined information has a wide range of application in many areas. Herein in the specification and appended claims, the DII is also referred to as Gait Energy or Gait Power or Gait Force.

It is a further objective of the present invention to provide for a powerful algorithm tools set for gait analysis with high time and spatial resolution. Embodiments of the present invention can be used for diagnosing gait impairment, assessing the effectiveness of therapeutic and rehabilitation treatment, identifying special medical conditions, sports medicine, athletic performance assessment and training, footwear and backpack design as well as for biometric security authentication.

Citation or identification of any reference in this section or any other section of this application shall not be construed as an admission that such reference is available as prior art for the present application.

SUMMARY OF THE INVENTION

Accordingly, it is an object of the present invention to provide a method of gait measurement using tri-axial accelerometer/gyro in mobile devices. In particular, the present invention relates to a method of gait measurement using tri-axial accelerometer/gyro in mobile devices for monitoring and improving the physical movement of a moving subject. In a first aspect of the present invention, there is provided a simple data analysis algorithm for gait measurement and diagnosis.

In a second aspect of the present invention there is provided a method for characterizing the movement of a subject comprising the use of a tri-axial accelerometer to formulate a signature based on measurements of walking, heaving and lateral movements of said subject, wherein said characterization further comprises a quantitative indicator indicating the power level dispensed by said subject to keep balance during said motion.

In a first embodiment of the second aspect of the present invention there is provided the method for characterizing the movement of a subject wherein the tri-axial accelerometer is located at or near the center of gravity of said subject.

In a second embodiment of the second aspect of the present invention there is provided the method for characterizing the movement of a subject wherein said subject can be a human or an animal.

In a third embodiment of the second aspect of the present invention there is provided the method for characterizing the movement of a subject wherein said signature is used in monitoring, diagnosing and improving the movement performance of said subject.

In a fourth embodiment of the second aspect of the present invention there is provided the method for characterizing the movement of a subject wherein said signature is used in monitoring the progress of physical rehabilitation and/or physical well being of said subject via the movement of said subject.

In a fifth embodiment of the second aspect of the present invention there is provided the method for characterizing the movement of a subject wherein said signature is used in the design and/or fitting of prosthesis for said subject.

In a sixth embodiment of the second aspect of the present invention there is provided the method for characterizing the movement of a subject wherein said signature is used as a biometric identifier of said subject.

In a seventh embodiment of the second aspect of the present invention there is provided the method for characterizing the movement of a subject wherein said signature is used as an indicator for physical impairment analysis of said subject, including but not limited to the diagnosis of kinesthetic problems for animals.

In an eighth embodiment of the second aspect of the present invention there is provided the method for characterizing the movement of a subject wherein said signature is used as an identifier for selecting subjects with better form of movement.

In a ninth embodiment of the second aspect of the present invention there is provided the method for characterizing the movement of a subject wherein said signature is used in design of footwear for said subject.

In a tenth embodiment of the second aspect of the present invention there is provided the method for characterizing the movement of a subject wherein said signature is used as an indicator in the fitting and selection of footwear for said subject.

In an eleventh embodiment of the second aspect of the present invention there is provided the method for characterizing the movement of a subject wherein said signature is used in the design of exercise equipment for said subject.

In a twelfth embodiment of the second aspect of the present invention there is provided the method for characterizing the movement of a subject wherein said signature is used in the design of backpacks and other forms of carry luggage for said subject.

In a thirteenth embodiment of the second aspect of the present invention there is provided the method for characterizing the movement of a subject wherein said method is implemented in software.

In a fourteenth embodiment of the second aspect of the present invention there is provided the method for characterizing the movement of a subject wherein said method is implemented in hardware.

In a third aspect of the present invention there is provided a method for characterizing the movement of a subject, comprising:
- based on measured acceleration data in all directions of said subject, using a gait cycle algorithm to measure a gait cycle of said subject, the gait cycle comprising at least one stride or at least two steps of said subject, wherein said at least one stride or at least two steps comprise at least one heel strike followed by at least one stance phase and at least one swing phase, and wherein said gait cycle algorithm time marks the at least one heel strike and at least one mid-single leg support that happens just before at least one toe-off;
- using a gait force spectrum algorithm to convert the acceleration data to a time dependent power spectrum, whereby the time dependent power spectrum is a Gait Force Spectrum; and
- using a gait force wheel algorithm to extract gait information from measured acceleration data to generate a Gait Force Wheel wherein said Gait Force Wheel uses a graphic representation to reflect at least one phase relationship between accelerations along different orientations.

In a first embodiment of the third aspect of the present invention there is provided the method for characterizing the movement of a subject wherein the at least one stance phase describes at least one sequence when at least one landing limb of said subject remains on a surface and pushes backwards against said surface until at least one toe-push starts the at least one swing phase.

In a second embodiment of the third aspect of the present invention there is provided the method for characterizing the movement of a subject wherein said acceleration data further comprise magnitude, timing, duration and direction of energy flow of said acceleration data.

In a third embodiment of the third aspect of the present invention there is provided the method for characterizing the movement of a subject wherein said time dependent power spectrum is expressed either in high time resolution determined by the acceleration data rate or by averaging over a preset interval.

In a fourth embodiment of the third aspect of the present invention there is provided the method for characterizing the movement of a subject wherein said at least one phase relationship between accelerations along different orientations comprises the phase relationship between surge (forward) and heave (vertical) acceleration orientations.

In a fifth embodiment of the third aspect of the present invention there is provided the method for characterizing the movement of a subject wherein said method further comprises using a 3-axes accelerometer attached to the center of gravity of said subject for measuring the acceleration data.

In a sixth embodiment of the third aspect of the present invention there is provided the method for characterizing the movement of a subject wherein said method has uses comprising characterizing normal gaits and abnormal gaits, the abnormal gaits further comprising Leg Length Discrepancy Syndrome, knee tremors, high knee lift, and gaits from hip replacement patients and Parkinson disease patients.

In an seventh embodiment of the third aspect of the present invention there is provided the method for characterizing the movement of a subject wherein said subject are human.

In a eighth embodiment of the third aspect of the present invention there is provided the method for characterizing the movement of a subject wherein said subject are juveniles.

In a fourth aspect of the present invention there is provided an apparatus for characterizing the movement of a subject, wherein the apparatus comprises one or more processors configured to execute a process comprising:
- based on measured acceleration data in all directions of said subject, using a gait cycle algorithm to measure a gait cycle of said subject, the gait cycle comprising at least one stride or at least two steps of said subject wherein said at least one stride or at least two steps comprise at least one heel strike followed by at least one stance phase and at least one swing phase, and wherein said gait cycle algorithm time marks the at least one heel strike and at least one mid-single leg support that happens just before at least one toe-off;
- using a gait force spectrum algorithm to convert the acceleration data to a time dependent power spectrum, whereby the time dependent power spectrum is a Gait Force Spectrum; and
- using a gait force wheel algorithm to extract gait information from measured acceleration data to generate a Gait Force Wheel wherein said Gait Force Wheel uses a graphic representation to reflect at least one phase relationship between accelerations along different orientations.

In a first embodiment of the fourth aspect of the present invention there is provided the apparatus for characterizing the movement of a subject wherein the at least one stance phase describes at least one sequence when at least one landing limb of said subject remains on a surface and pushes backwards against said surface until at least one toe-push starts the at least one swing phase.

In a second embodiment of the fourth aspect of the present invention there is provided the apparatus for characterizing the movement of a subject wherein said acceleration data further comprise magnitude, timing, duration and direction of energy flow of said acceleration data.

In a third embodiment of the fourth aspect of the present invention there is provided the apparatus for characterizing the movement of a subject wherein said time dependent power spectrum is expressed either in high time resolution determined by the acceleration data rate or by averaging over a preset interval.

In a fourth embodiment of the fourth aspect of the present invention there is provided the apparatus for characterizing the movement of a subject wherein said at least one phase relationship between accelerations along different orientations comprising the phase relationship between surge (forward) and heave (vertical) acceleration orientations.

In a fifth embodiment of the fourth aspect of the present invention there is provided the apparatus for characterizing the movement of a subject wherein said apparatus further comprises a 3-axes accelerometer for measuring the acceleration data when attached to the center of gravity of said subject.

In a sixth embodiment of the fourth aspect of the present invention there is provided the apparatus for characterizing the movement of a subject wherein said apparatus has uses comprising characterizing normal gaits and abnormal gaits, the abnormal gaits further comprising Leg Length Discrepancy Syndrome, knee tremors, high knee lift, and gaits from hip replacement patients and Parkinson disease patients.

In an seventh embodiment of the fourth aspect of the present invention there is provided the apparatus for characterizing the movement of a subject wherein said subject are human.

In a eighth embodiment of the fourth aspect of the present invention there is provided the apparatus for characterizing the movement of a subject wherein said subject are juveniles.

Those skilled in the art will appreciate that the invention described herein is susceptible to variations and modifications other than those specifically described.

The invention includes all such variation and modifications. The invention also includes all of the steps and features referred to or indicated in the specification, individually or collectively, and any and all combinations or any two or more of the steps or features.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the invention and apply throughout. Unless otherwise defined, all other technical terms used herein have the same meaning as commonly understood to one of ordinary skill in the art to which the invention belongs.

Other aspects and advantages of the invention will be apparent to those skilled in the art from a review of the ensuing description.

BRIEF DESCRIPTION OF THE DRAWINGS

The above and other objects and features of the present invention will become apparent from the following description of the invention, when taken in conjunction with the accompanying drawings.

FIG. 7c shows the WHLS of a 23-year-old male, where the DII is 1186, and the test subject had never exercised and had had a case of obesity.

FIG. 9a shows the WHLS of a 40-year-old female in flat heel shoes, the DII being 246.

FIG. 11b shows the WHLS of the same subject as FIG. 11a ascending a staircase, the DII being 274.

DETAILED DESCRIPTION OF THE INVENTION

Figure 1:
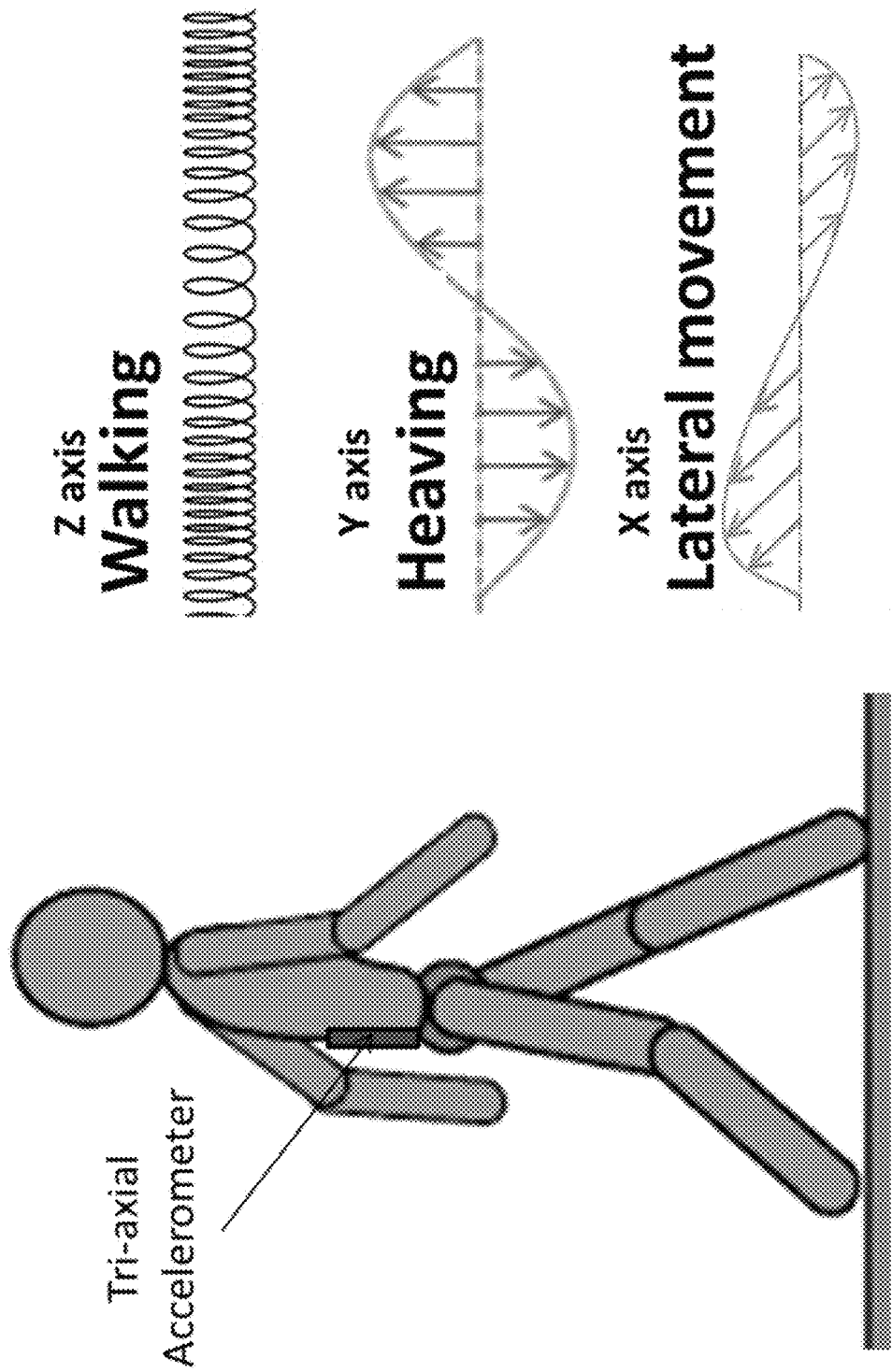
FIG. 1 shows the placement of the device on human during measurement and the three waveforms associated with the motion.

The present invention is not to be limited in scope by any of the specific embodiments described herein. The following embodiments are presented for exemplification only.

In a first aspect of the present invention, there is provided a simple data analysis algorithm for gait measurement and diagnosis.

In a second aspect of the present invention there is provided a method for characterizing the movement of a subject comprising the use of a tri-axial accelerometer to formulate a signature based on measurements of walking, heaving and lateral movements of said subject, wherein the signature further comprising a quantitative indicator indicating the power level dispensed by said subject to keep balance during said motion.

In a first embodiment of the second aspect of the present invention there is provided the method for characterizing the movement of a subject wherein the tri-axial accelerometer is located at the center of gravity of said subject.

In a second embodiment of the second aspect of the present invention there is provided the method for characterizing the movement of a subject wherein said subject comprising human and animal.

In a third embodiment of the second aspect of the present invention there is provided the method for characterizing the movement of a subject wherein said signature is used in monitoring, diagnosing and improving the movement performance of said subject.

In a fourth embodiment of the second aspect of the present invention there is provided the method for characterizing the movement of a subject wherein said signature is used in monitoring the progress of physical rehabilitation and/or physical well-being of said subject via the movement of said subject.

In a fifth embodiment of the second aspect of the present invention there is provided the method for characterizing the movement of a subject wherein said signature is used in the design and/or fitting of prosthesis for said subject.

In a sixth embodiment of the second aspect of the present invention there is provided the method for characterizing the movement of a subject wherein said signature is used as biometric identifier of said subject.

In a seventh embodiment of the second aspect of the present invention there is provided the method for characterizing the movement of a subject wherein said signature is used as indicator for physical impairment analysis of said subject, including but not limited to the diagnosis of kinesthetic problems for animals.

In an eighth embodiment of the second aspect of the present invention there is provided the method for characterizing the movement of a subject wherein said signature is used as identifier for selecting subjects with better form of movement.

In a ninth embodiment of the second aspect of the present invention there is provided the method for characterizing the movement of a subject wherein said signature is used in design of footwear for said subject.

In a tenth embodiment of the second aspect of the present invention there is provided the method for characterizing the movement of a subject wherein said signature is used as indicator in the fitting and selection of footwear for said subject.

In an eleventh embodiment of the second aspect of the present invention there is provided the method for characterizing the movement of a subject wherein said signature is used in the design of exercise equipment for said subject.

In a twelfth embodiment of the second aspect of the present invention there is provided the method for characterizing the movement of a subject wherein said signature is used in the design of backpacks and other forms of carry luggage for said subject.

In a thirteenth embodiment of the second aspect of the present invention there is provided the method for characterizing the movement of a subject wherein said method is implemented in software.

In a fourteenth embodiment of the second aspect of the present invention there is provided the method for characterizing the movement of a subject wherein said method is implemented in hardware.

Walking, Heaving, Lateral-Movement Signature (WHLS)

In one embodiment of the present invention there is provided a real-time diagnosis technique with a tri-axial accelerometer embedded in a smart phone or a stand-alone tri-axial accelerator package with power and data acquisition components. In most cases, where the translational motions are dominant, the tri-axial accelerometer data will suffice. However, for more accurate measurement, a tri-axial accelerometer/gyro device should be used to acquire movements in all six degrees of freedom (three translations: sway, surge, heave and three rotations: pitch, roll and yaw). In running or walking, an object moves periodically in all three directions: heave (up/down), sway (side/side) and surge (forward/backward) shown in FIG. 1. Consider the variation of acceleration along these directions, the heave (up/down) and sway (side/side) acceleration act like a transverse wave (i.e. amplitude perpendicular to the movement direction), while the surge (forward/backward) acceleration acts like a longitudinal wave (amplitude parallel to movement direction). Therefore, the motion of running or walking can be expressed as a linear combination of these three waveforms. Instead of measuring the displacement, a more relevant and direct quantity to measure is the acceleration. During test, the sensor unit will be strap mounted to the center of gravity of the subject. For human body, it will be placed tightly against the center of the lower back. Data collection rate is carried out at 100 Hz. During a set of test, the subject will instructed to carry out physical activities such as walking, running, ascending and descending stairs, etc. for a short period of time of approximately 20 seconds. Data taken during the first and last five seconds will be discarded because they are not at a steady state. Only the data taken under steady state will be used. Each set of data consists of three acceleration values, $a_{1x}$, $a_{1y}$ and $a_{1z}$ shown in FIG. 2, corresponding to the three acceleration components along the respective axes. The magnitude of each component will be plotted in a Cartesian coordinate. This plot is equivalent to plot the time evolving trajectory of the net total acceleration vector in a polar coordinate. It will yield a three dimensional trajectory, named WHLS (Walking, Heaving and Lateral movement Signature). Its shape is unique for each individual. With the sensitivity of tri-axial accelerometer of approximate 0.003 g where g=9.8 ms$^{-2}$), a 0.001 m resolution limit in displacement within 50 msec time interval can be achieved. The high sensitivity is capable to reveal slight movement anomaly due to the physical condition of the person, such as back pain, weak knees, limp, discomfort in footwear, carrying a load, etc. Embodiments of the present invention have compiled data from various individuals engaged in various physical activities.

Figure 2:
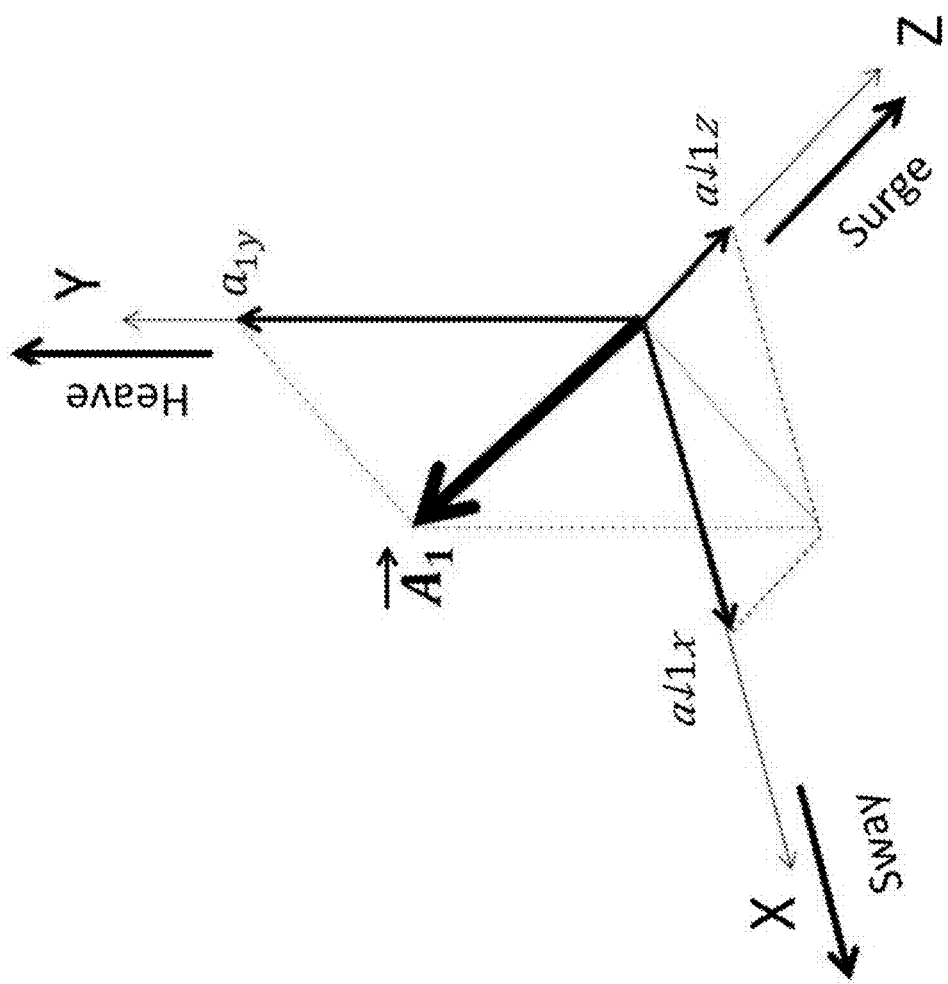
FIG. 2 shows the measured acceleration in a Cartesian coordinate at time $t_1$. The three axes X, Y, Z represent sway, heave and surge movement, respectively.
Figure 3:
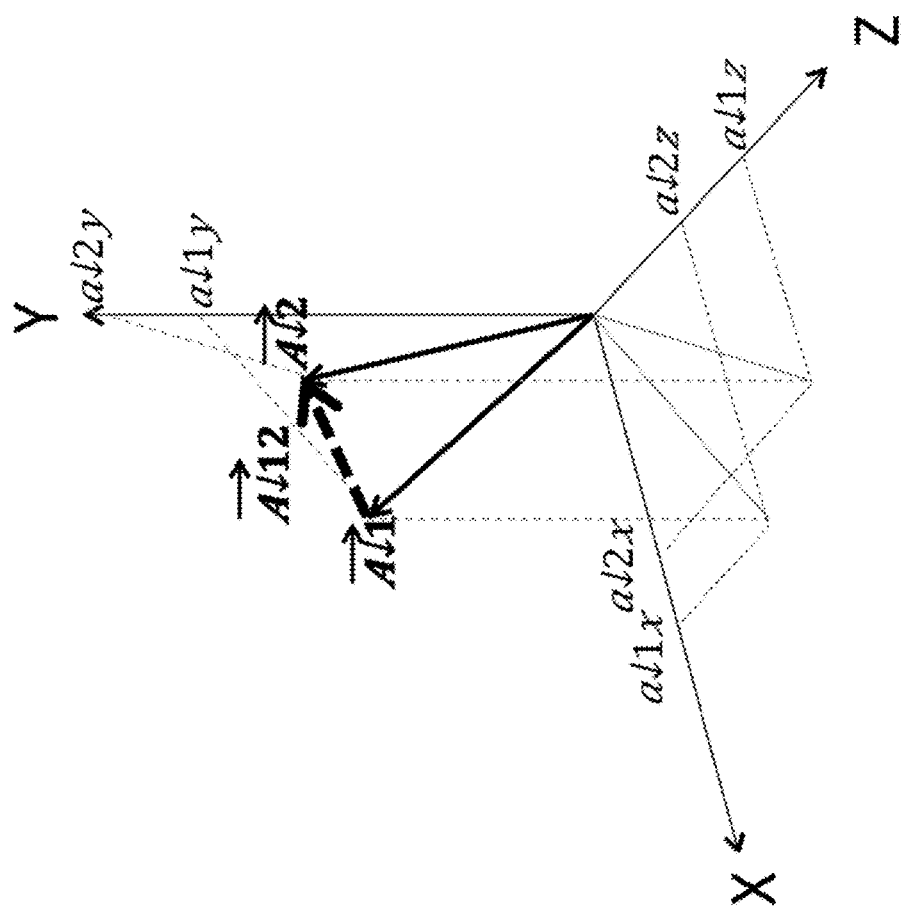
FIG. 3 shows the measured acceleration vector $\vec{A}_2$ at time $t_2$ and its relationship to vector $\vec{A}_{12}$, the vector corresponding to the movement of center of gravity of the test subject.
Figure 4:
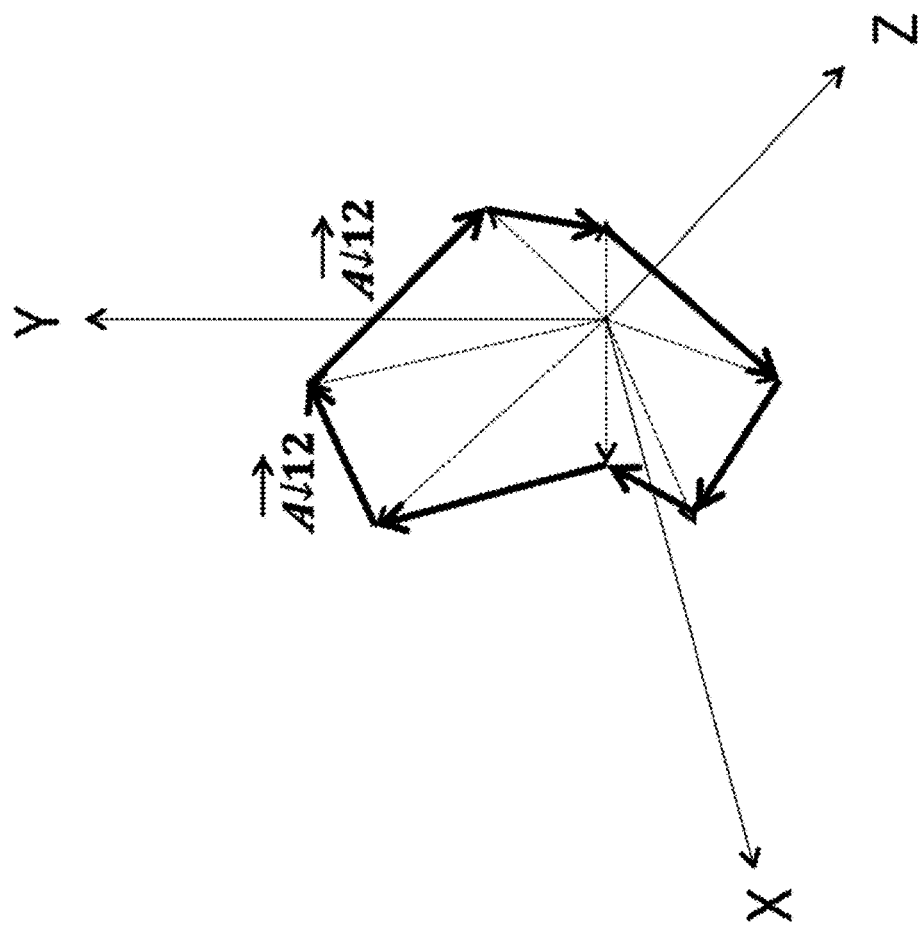
FIG. 4 shows the trace of vectors of the movement of the center of gravity of the test subject.

More precisely as shown in FIG. 2, vector $\vec{A}_1$ is the summation of the three components $a_{1x}$, $a_{1y}$ and $a_{1z}$ taken at time $t_1$. Second set of data acquisition takes place at time point $t_2$ after a time interval $\Delta t_{12}$. The new set of acceleration components is labeled as $a_{2x}$, $a_{2y}$ and $a_{2z}$. The vector sum of these components is vector $\vec{A}_2$, shown in FIG. 3. Therefore, during this time interval, the acceleration vector of the center of gravity of the test subject is $\vec{A}_{12}$, where vectors $\vec{A}_1 + \vec{A}_{12} = \vec{A}_2$. This will continue throughout the movements and the vectors $\vec{A}_{ij}$ will eventually form a continuous trace to represent the trajectory of the center of gravity of the moving test subject in the acceleration coordinate space as shown in FIG. 4. If the subject is moving along a straight line at a constant velocity, the net sum of all vectors of each cycle must equal to zero or $\Sigma_i \vec{A}_i$, according to Newton's Laws of Motion. However, the total acceleration of the movement of the center of gravity of the subject under test, or $\Sigma \vec{A}_{ij}$, is finite. The result can be used to assess valuable information regarding gait. Data analysis can be divided into two parts: (1) 3D graphic trace of the acceleration trajectory or the Walk Heave Lateral Movement Signature (WHLS) and (2) quantitative results relating to the subject's ability to keep balanced during motion.

Figure 5:
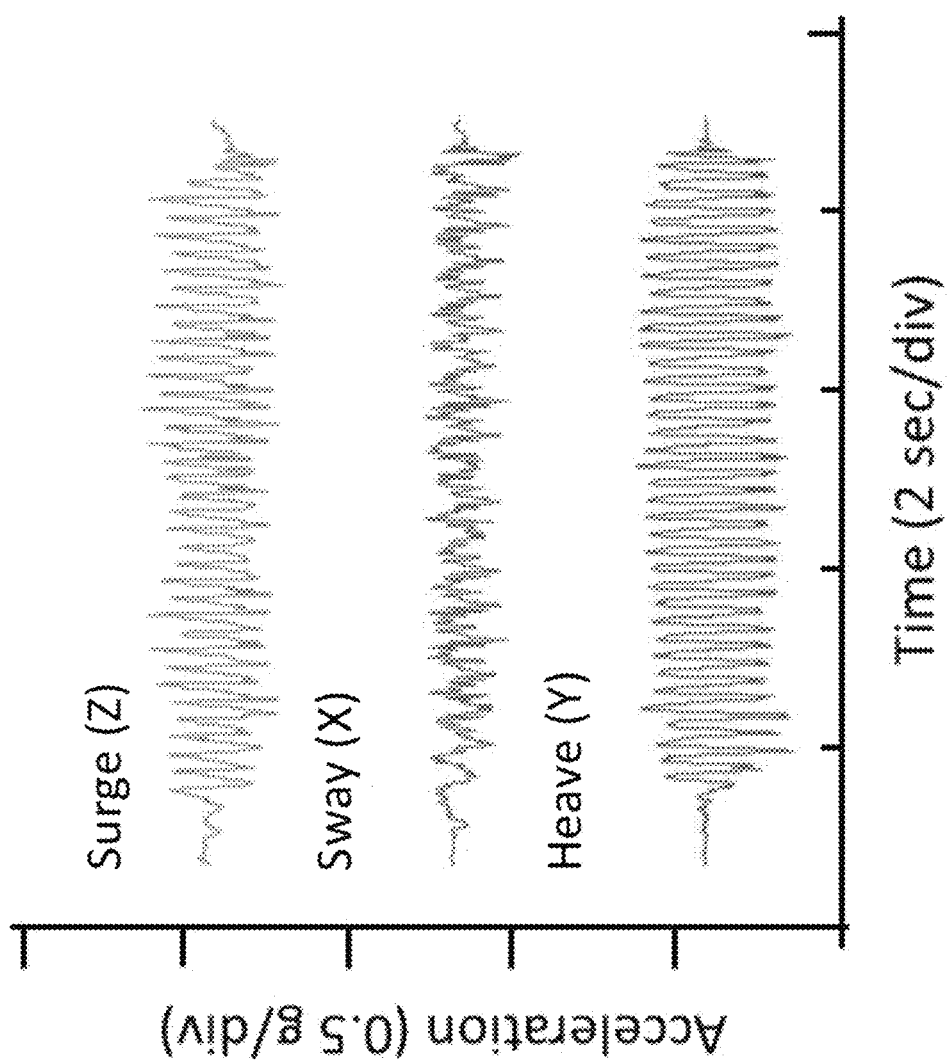
FIG. 5 shows the raw data of measured acceleration along three axes of the test subject.
Figure 6:
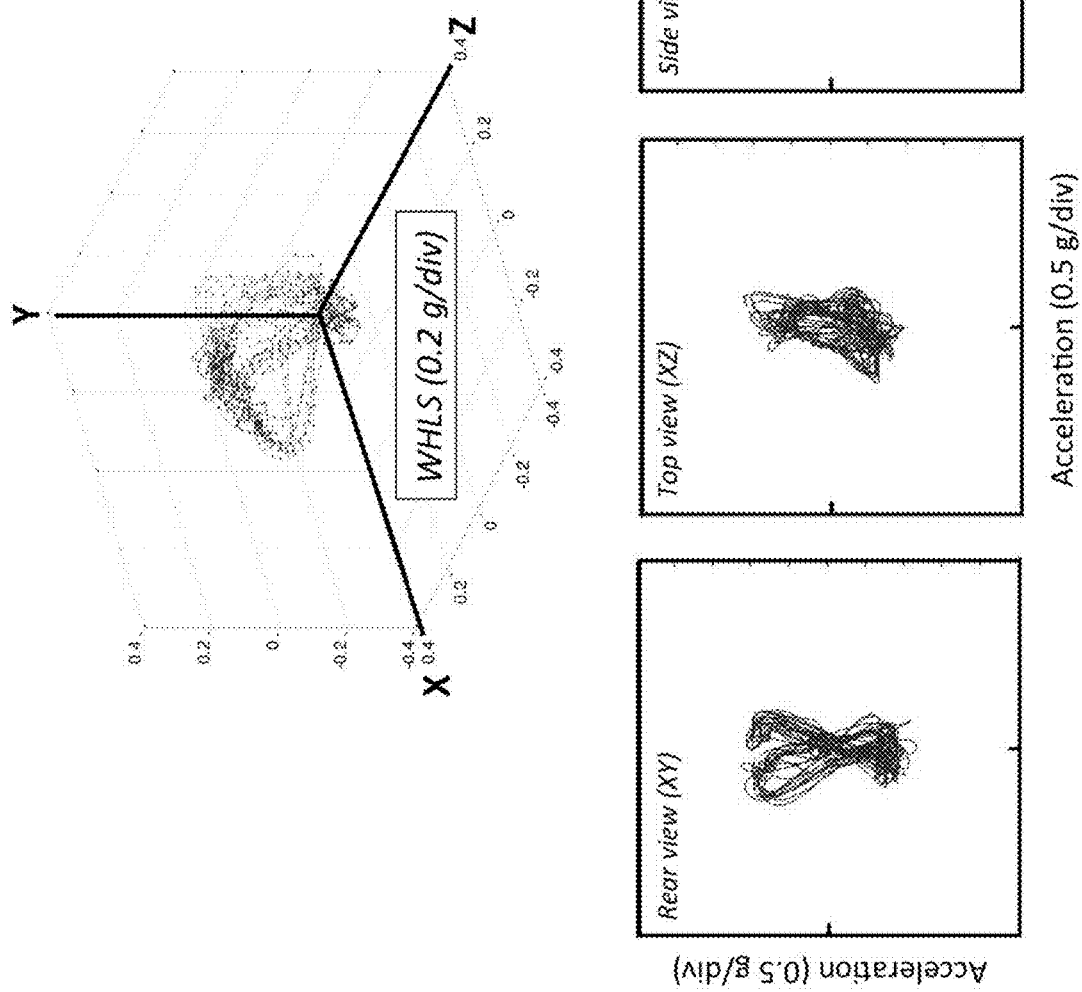
FIG. 6 shows a typical Walking Heaving Lateral-Movement Signature (WHLS) pattern and views from three direction of the test subject.

FIG. 5 shows a plot of the raw acceleration data along 3 axes. The data, when plotted in a 3D polar coordinate, yields a 3D trace of the acceleration vector trace over the period of walking as shown in FIG. 6a. 2D views from three different directions are also shown in FIG. 6b. The pattern is named "Walking Heaving Lateral movement Signature", or WHLS. It is unique for each individual person and for different movement. It can be used for biometric identification and diagnosis of gait imperfection. Traditional gait measurement relies solely on analyzing the amplitude and frequency of periodic movement. The phase relationships between different movements are ignored, thus missing valuable biomechanical information. This approach takes the relative phase difference between periodic movements along three axes into account to unveil a wealth of useful information including small irregular features related to gait.

Following figures show a collection of WHLS patterns of different individuals with same movement (i.e. walking) or same individual in different movements (e.g. normal walking vs. ascending on staircase, with or without bearing a load on the back), or in different foot wears such as heel less shoes, high heels, etc. The uniqueness clearly supports the use of such patterns for biometrics and many other applications.

Important features include the following.

Figure 7A:
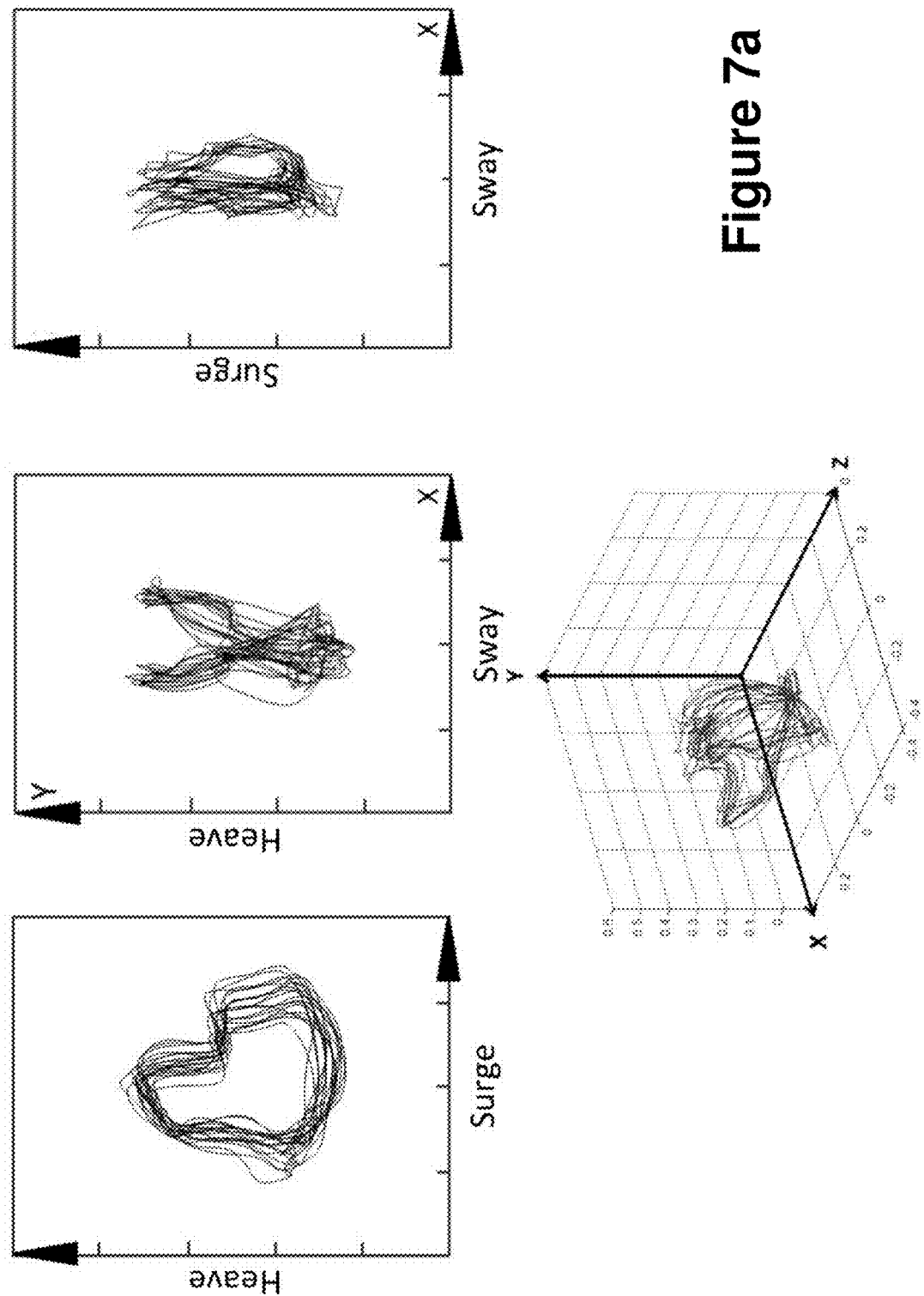
FIG. 7a shows the WHLS of a 27-year-old male, with the Dynamic Instability Index (DII) being 259.
Figure 7B:
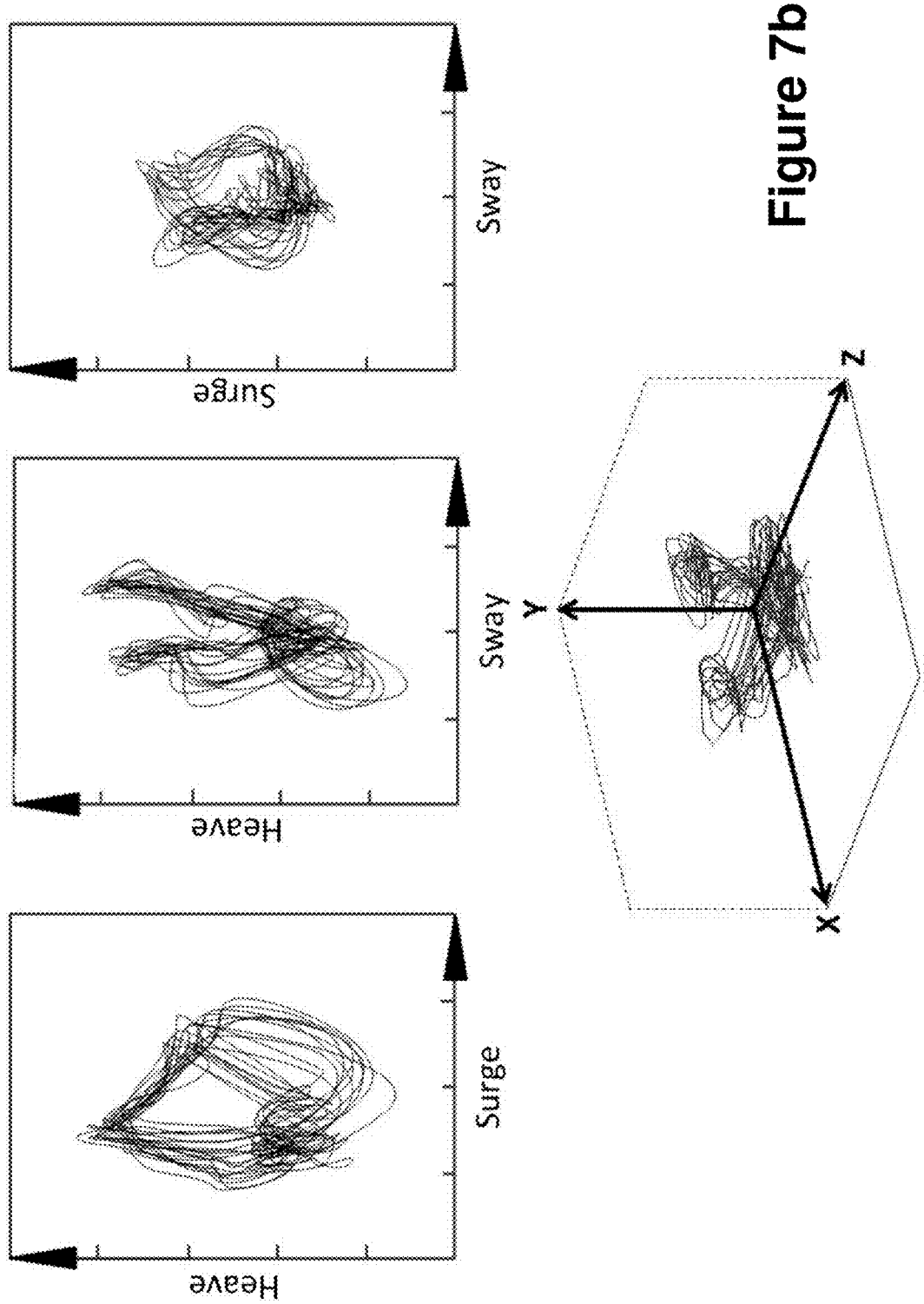
FIG. 7b shows the WHLS of a 68-year-old male, where the DII is 416, and the asymmetry in the YX view is caused by a weak right knee.

Comparing FIGS. 7a, 7b and 7c:

These three WHLS patterns show the difference between the individuals with difference age and level of physical fitness. The individual in FIG. 7a is a 27-year-old male with a routine regiment of exercise and balanced diet. His physical fitness is reflected in the tight and well-defined WHLS pattern. Another prominent feature is seen in the X/Y (or lateral movement/heave) view that shows nearly symmetric and alternate heave movement in left and right. FIG. 7b shows the WHLS pattern of a 68-year-old male. The pattern is much less well defined. There is clearly asymmetry between left and right movements in particularly in the Y-X plot. The behavior is caused by weak left knee. This subject has been monitored for over 10 months with any noticeable change in this distinctive feature. FIG. 7c shows the WHLS of a 23-year-old male who is completely out of shape and has shown a sign of obesity. The lack of fitness is reflected in the pattern which is loose and ill defined. This group of results suggests the use of WHLS as a simple way to assess one's fitness.

Figure 8A:
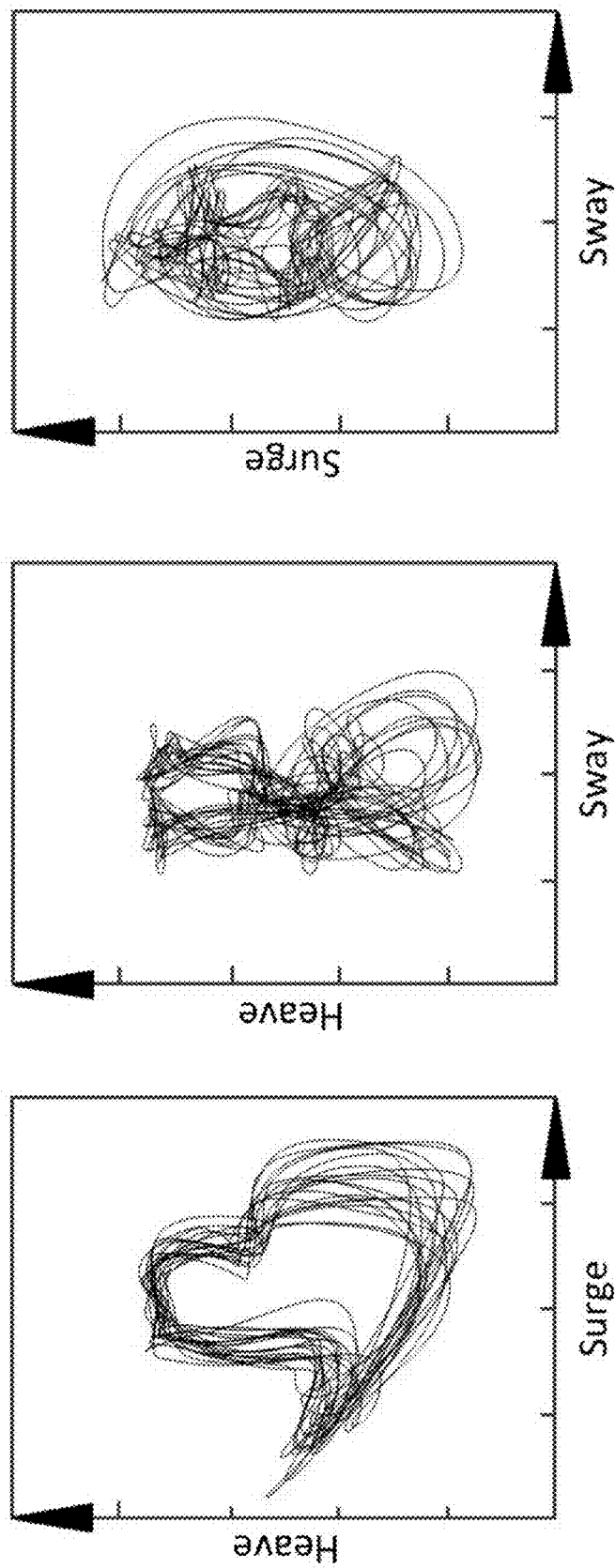
FIG. 8a shows the WHLS of a 24-year-old male with both shoes, the DII being 754.
Figure 8B:
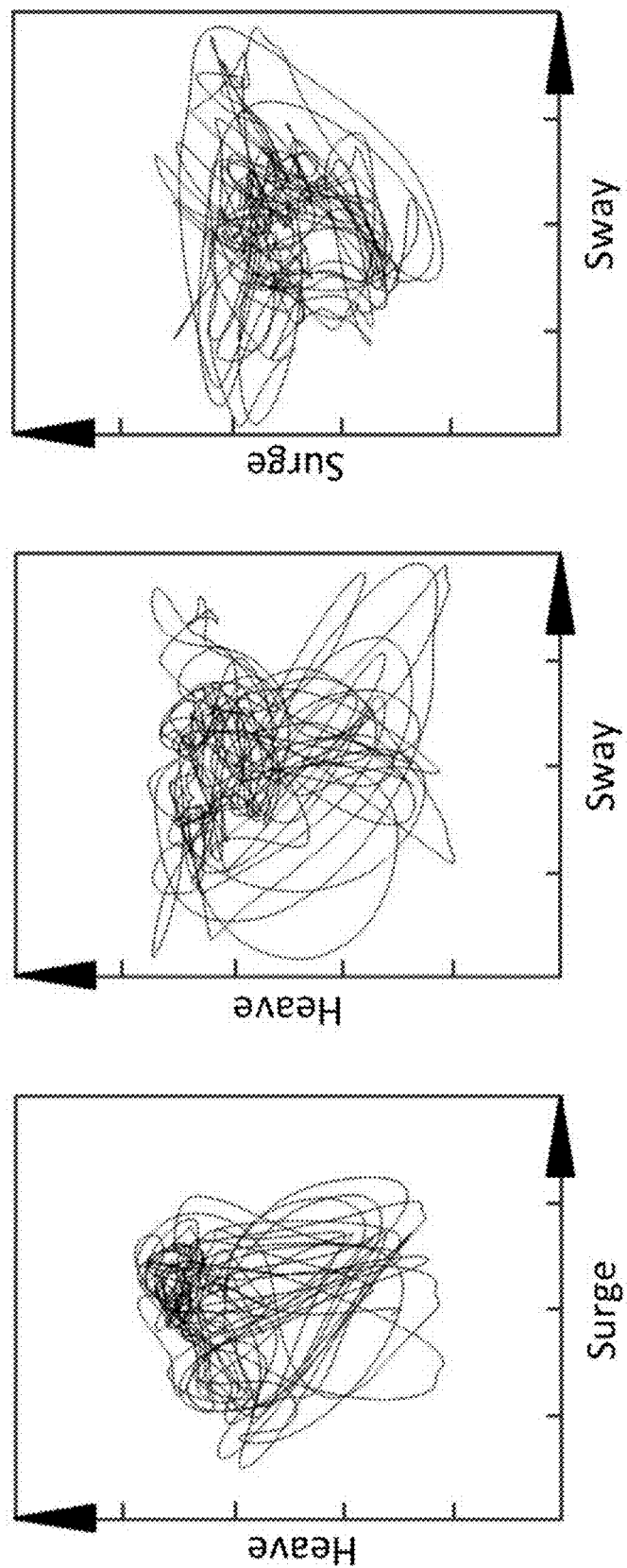
FIG. 8b shows the WHLS of the same subject as in FIG. 8a walking in only one shoe, the DII being 914.
Figure 8C:
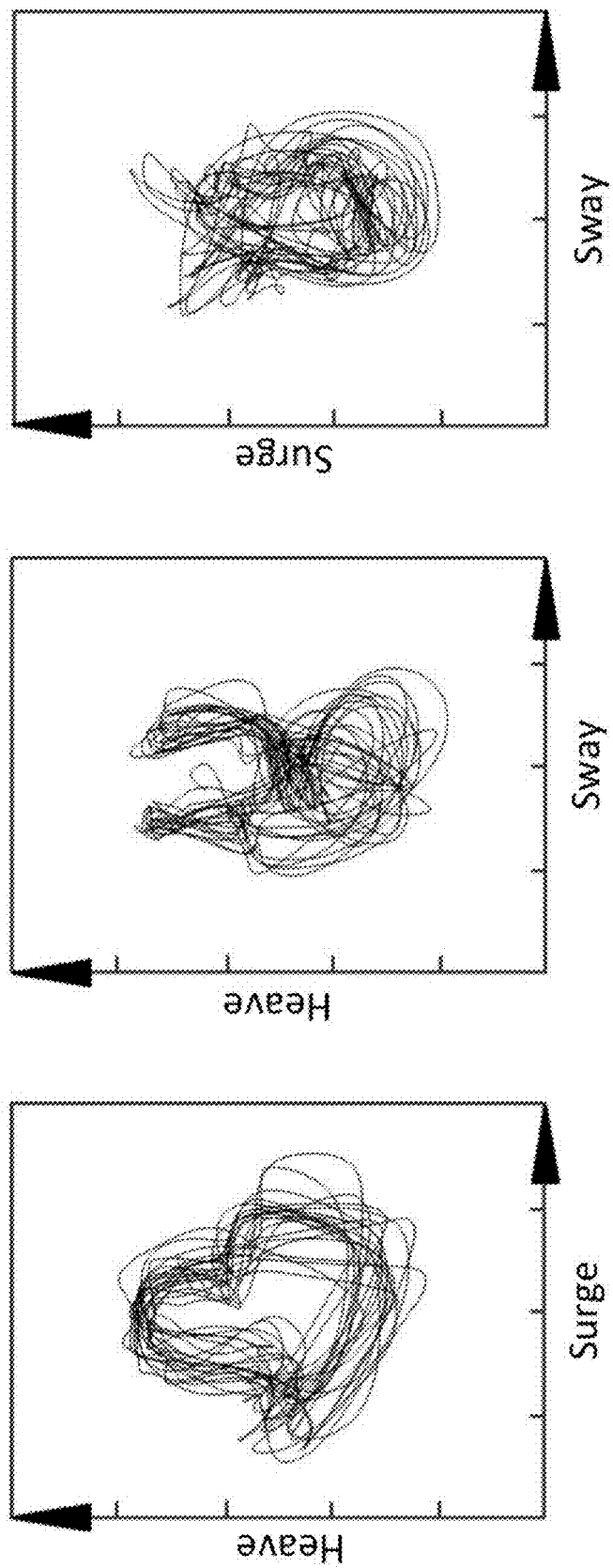
FIG. 8c shows the WHLS of the same subject as in FIG. 8a walking without shoes, the DII being 617.

Comparing FIGS. 8a, b, c:

These WHLS patterns depict the same individual under different walking conditions. FIG. 8a represents a 2D WHLS pattern taken under normal walking condition with shoes on both feet. FIG. 8b is the WHLS pattern taken under the same condition except the subject was wearing only one shoe. As a result, this imbalance immediate translates into a chaotic WHLS pattern in which the periodic pattern is no longer recognizable. However, when the same subject was walking with both shoes removed, the balance was largely recovered as well as the WHLS pattern shown in FIG. 8c. The dramatic change shows the high sensitivity of WHLS as a tool to detect any gait imperfection due to discomfort in feet and footwear.

Figure 9B:
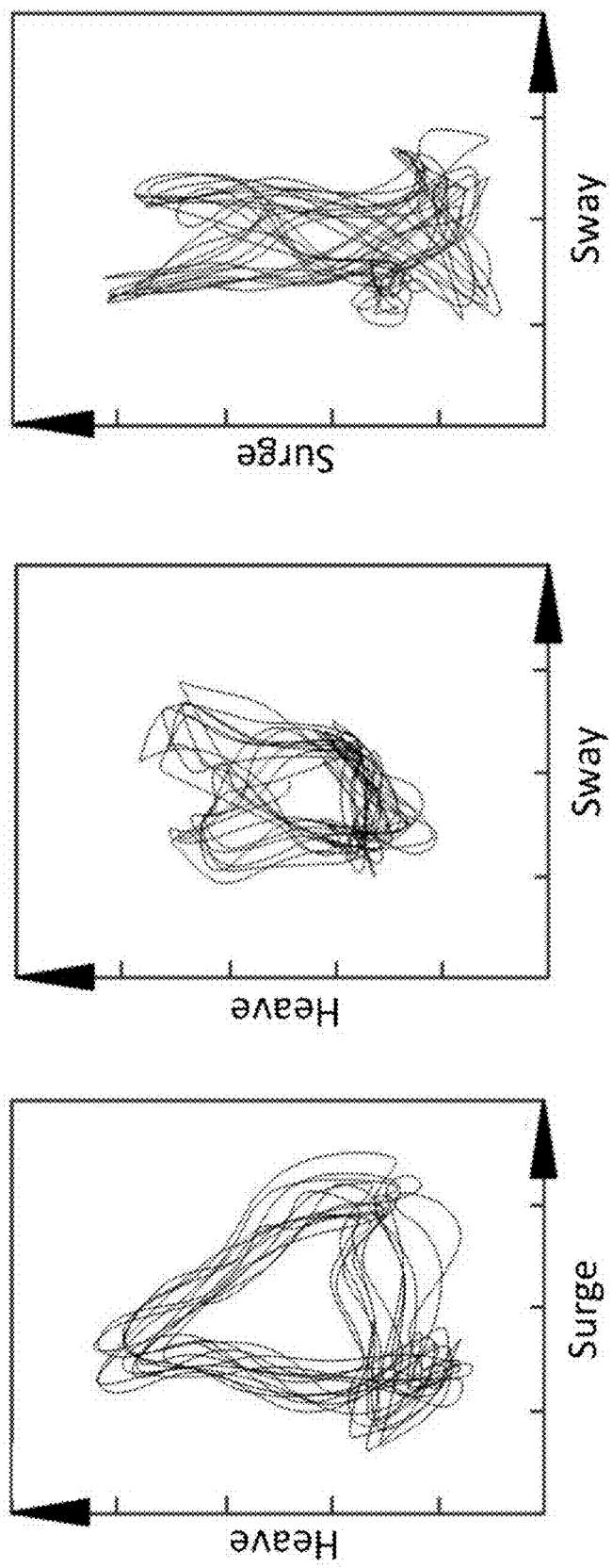
FIG. 9b shows the WHLS of the same subject as in FIG. 9a except wearing 2" high heel shoes, the DII being 567.

Comparing FIGS. 9a, b:

These two WHLS patterns depict a middle-aged lady walking in flat heeled feet (FIG. 7a) and in high heel. This subject wears high heel in rare occasions. Results show a much higher (5 times higher) level of power needed to keep balanced in high heels. It points out the effectiveness of WHLS pattern as an effective way for footwear design.

Figure 10A:
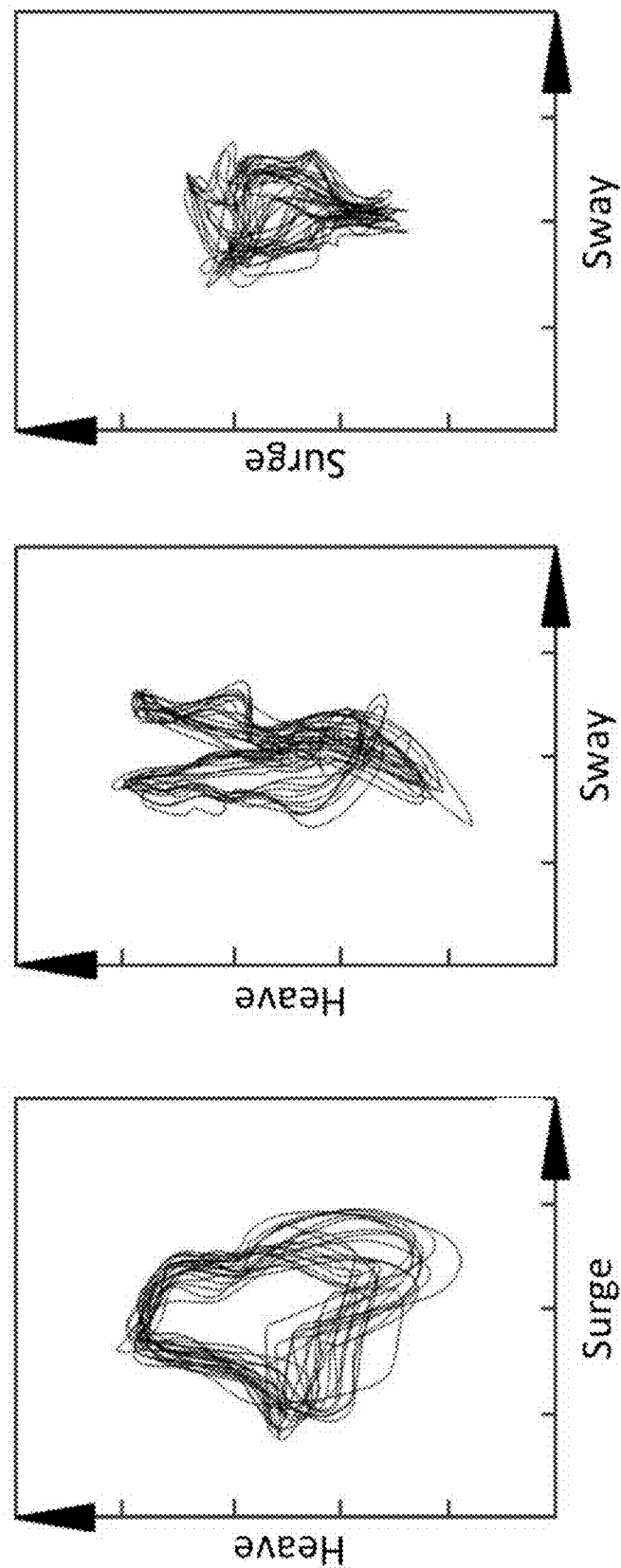
FIG. 10a shows the WHLS of a 24-year-old male carrying a 6 kg backpack on both shoulders; the DII being 355.
Figure 10B:
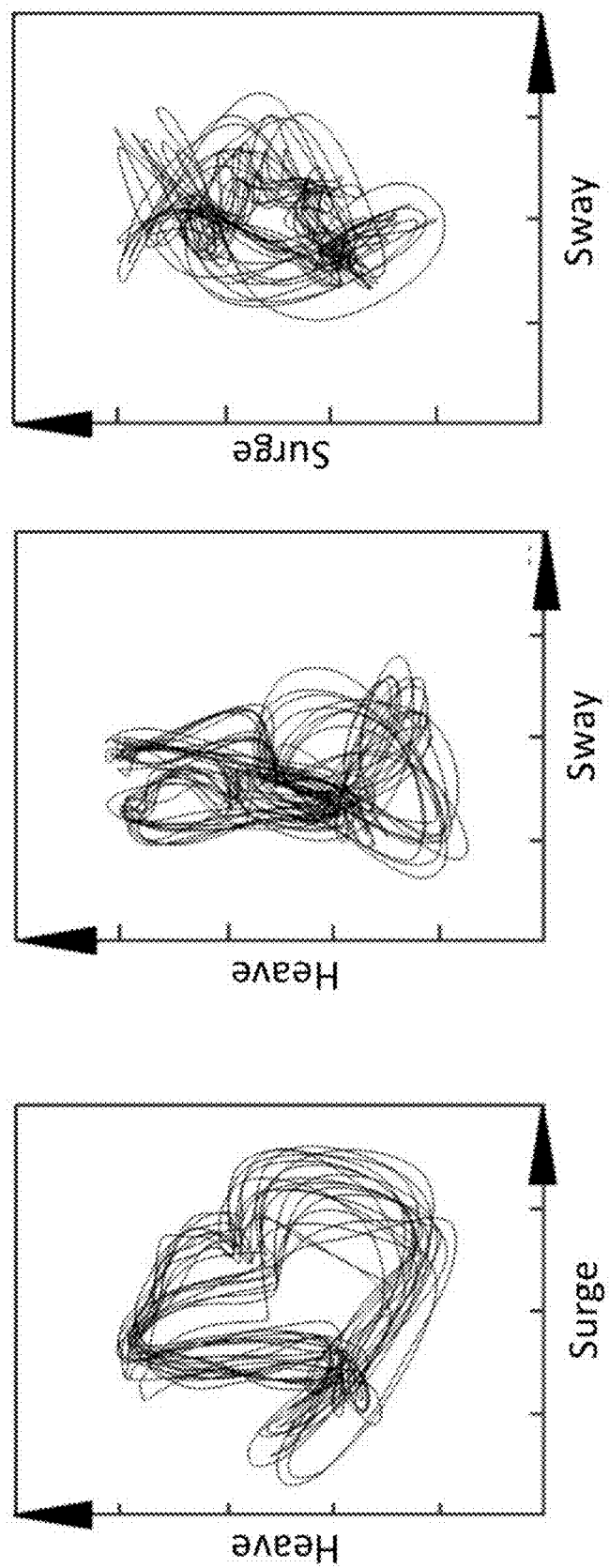
FIG. 10b shows the WHLS of a 24-year-old male carrying a 6 kg backpack with one shoulder; the DII being 796.

Comparing FIGS. 10a, b:

These two figures depict WHLS patterns of a person carrying a backpack with a 6 kg load either carried with both shoulders (FIG. 10a) or slinging across one shoulder (FIG. 10b). The results clear indicate the two shoulders style is more efficient and healthy. This approach can be used to improve backpack design.

Figure 11A:
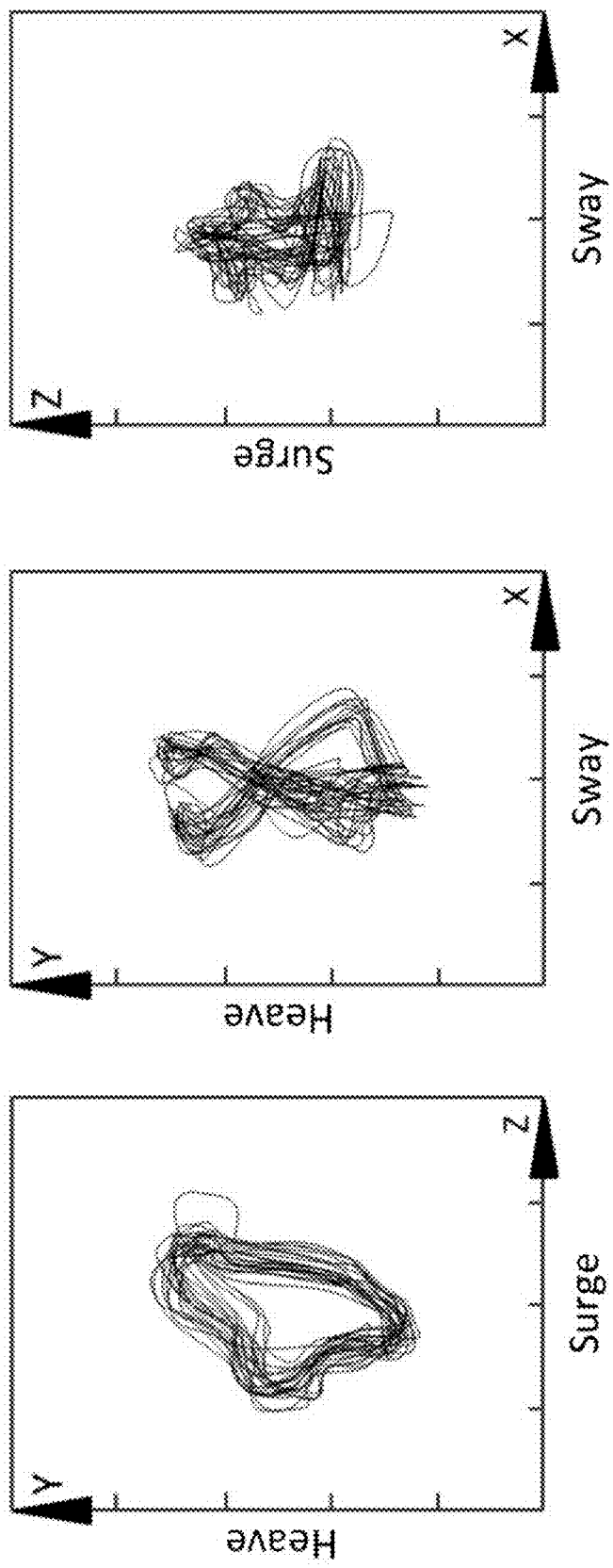
FIG. 11a shows the WHLS of a 24-year-old female walking; the DII being 279.

Comparing FIGS. 11a, b, c

Figure 11C:
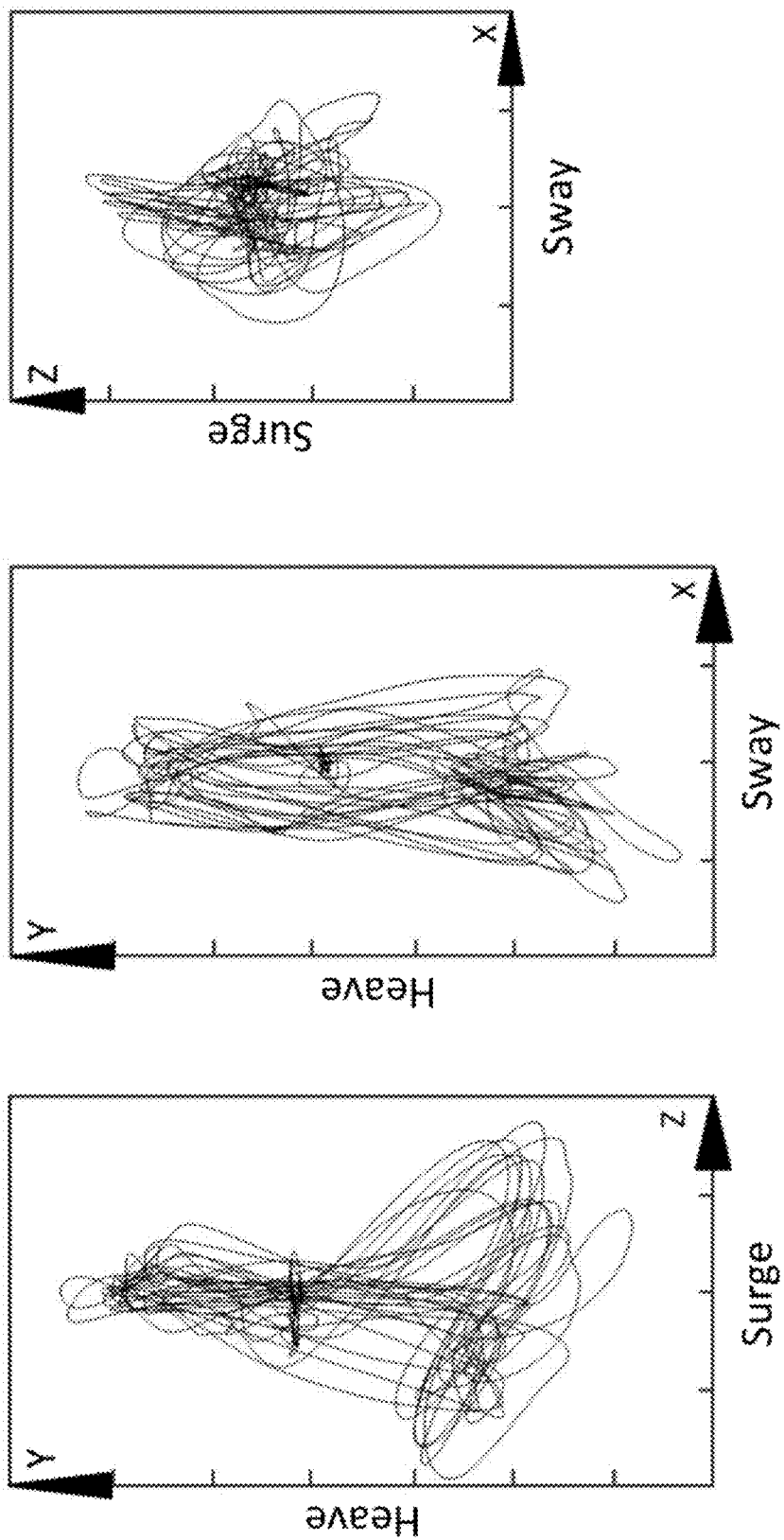
FIG. 11c shows the WHLS of the same subject as FIG. 11a descending from a staircase, the DII being 1501.

These three sets of 2D WHLS patterns systematically compare a person normal walking (FIG. 11a), ascending staircase (FIG. 11b), and descending staircase (FIG. 11c). Results show a distinctive difference between them with the descending movement requiring higher power level to keep balance. Another feature worthy to point out is the X/Y view of ascending WHLS. Similar to the normal walking case, it also has two finger-like features corresponding to the periodic leg movement. However, their polarity is opposite as they point downward instead of pointing upward as in normal walking. This is due to the heel/toe action in the normal walking, yet this action is missing in the ascending movement.

Quantitative Analysis of the WHLS Data—Dynamic Instability Index (DII)

To further understand the WHLS patterns, one embodiment of the present invention provides an algorithm to calculate the amount of power level required to keep balance. The value that is adjusted to a range between zero and a few thousand for practical purpose is named Dynamic Instability Index (DII), or Gait Energy, Gait Force or Gait Power, although the quantity is a measure of power level. For the same speed, a low DII signals better fitness and a more effective gait. A high DII implies the opposite. This algorithm extracts the power requirement from the WHLS pattern by performing a double integration along the acceleration trajectory.

A Detailed Process Description

For each time interval, the center of gravity of the individual under test proceeds along acceleration vector $\vec{A}_{ij}$. For very short time interval, the acceleration can be assumed to have a linear time dependence, namely, $\vec{A}_{ij}=k_{ij}t$, where $k_{ij}$ is the slope of the vector $\vec{A}_{ij}$ in the acceleration-time space. The slope $k_{ij}$ can be determined from the coordinates of vectors $\vec{A}_i$ and $\vec{A}_j$ as:

$$k_{ij} = \frac{[(a_{xj}-a_{xi})^2 + (a_{yj}-a_{yi})^2 + (a_{zj}-a_{zi})^2]^{\frac{1}{2}}}{\Delta t_{ij}}.$$

The distance $S_{ij}$ that the center of gravity travels during the time interval $\Delta t_{ij}$, which happens to be the reciprocal of the data rate, can be obtained by performing a double integral:

$$S_{ij} = \int\int_{t_i}^{t_j} \vec{A}_{ij} dt dt = \frac{1}{6}k_{ij}\Delta t_{ij}^3.$$

By substituting $\vec{A}_{ij}=k_{ij}t$ into the double integral of the last equation, the distance can be calculated by $$S_{ij} = \frac{1}{6}k_{ij}\Delta t_{ij}^3.$$

Consequently, the amount of work done during this time can be obtained by $$W_{ij} = F(t)S_{ij} = \frac{F(t)k_{ij}\Delta t_{ij}^3}{6}.$$

For simplicity, due to the short time interval, it is assumed that the force F to be independent of time and simply F=m<a>, where m is the mass and <a> is the average acceleration during the time interval. Therefore, the total work performed or the energy spent during the time can be obtained by taking the summation of forces associated with individual segments along the trajectory. For convenience, one embodiment of the present invention further divides this value by the total measurement time. The result is the power level that is needed to keep the individual under test in balance. In this formulation, the mass m is taking as a constant and remains the same for all test subjects. In order to make the result in a proper range, this embodiment of the present invention multiply the number by a constant bring the range to a few hundred under normal circumstances. It is named as Dynamic Instability Index (DII), or Gait Power (or sometimes misnamed as Gait Energy although the quantity is a measurement of power level). Higher DII indicates higher power level to keep balanced and associated with less physical fitness and vice versa. Some representative DIIs for various cases are listed in Table 1 for reference. The calculation time is just a fraction of a second. Its magnitude provides a quantitative measure of the gait quality.

TABLE 1

Some representative DIIs for various cases.

| FIG. | Age | Gender | Activity | Fitness level | DII |
|---|---|---|---|---|---|
| 7a | 28 | M | Normal walking | Excellent | 259 |
| 7b | 68 | M | Normal walking | Average | 416 |
| 7c | 23 | M | Normal walking | Poor | 1186 |
| xxx | 22 | M | Normal walking | Poor | 826 |
| xxx | 23 | F | Normal walking | Good | 246 |
| xxx | 54 | M | Normal walking | Average | 426 |
| xxx | 63 | M | Normal walking | Average | 395 |
| 9a | 40 | F | Flat heel | Excellent | 246 |
| 9b | 40 | F | High heel | Excellent | 567 |
| 10a | 24 | M | Load both shoulders | Average | 355 |
| 10b | 24 | M | Load one shoulder | Average | 796 |
| 11b | 23 | F | Ascending stairs | Good | 274 |
| 11c | 23 | F | Descending stairs | Good | 1507 |

The measurement described here use a 100 Hz data rate that proves to be adequate for studying human gait. However, if the gait consists of sudden spikes such as horse galloping, devices with higher data rate must be used. Though the analysis algorithm remains the same.

Figure 12:
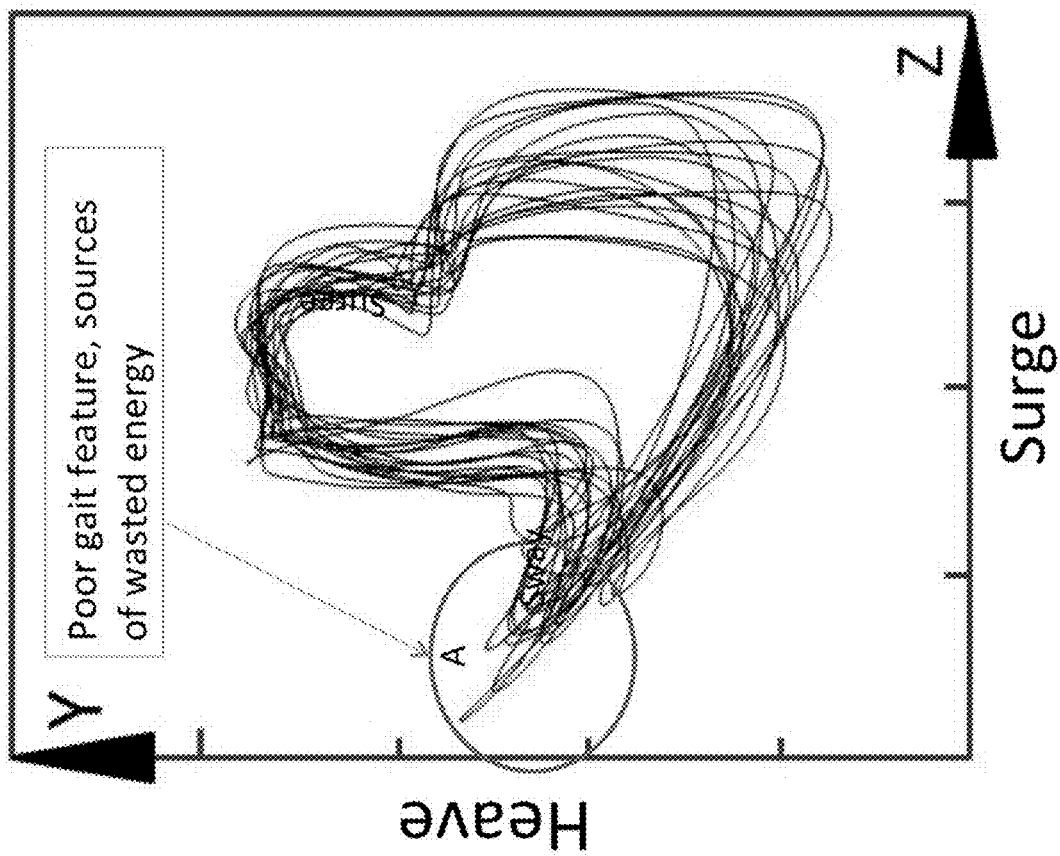
FIG. 12 shows the surge/heave view of the WHLS of a 27-year-old male, where the circled feature indicates wasted movement in gait.

This analysis points out that an ideal gait is one with minimum energy spent during each cycle. The WHLS pattern should be smooth without any extra features. An example shown in FIG. 12 depicts the ZY view (i.e. surge/heave) of a WHLS trace. It is far from being a smooth oval or circle. It has a major feature at locations A that represents a motion of wasted energy. By combining WHLS measurement with frame-by-frame motion analysis, it is possible to identify the cause of this feature and eliminate it. Thus, this approach can be used as an effective and systematic tool to improve one's gait.

Figure 13:
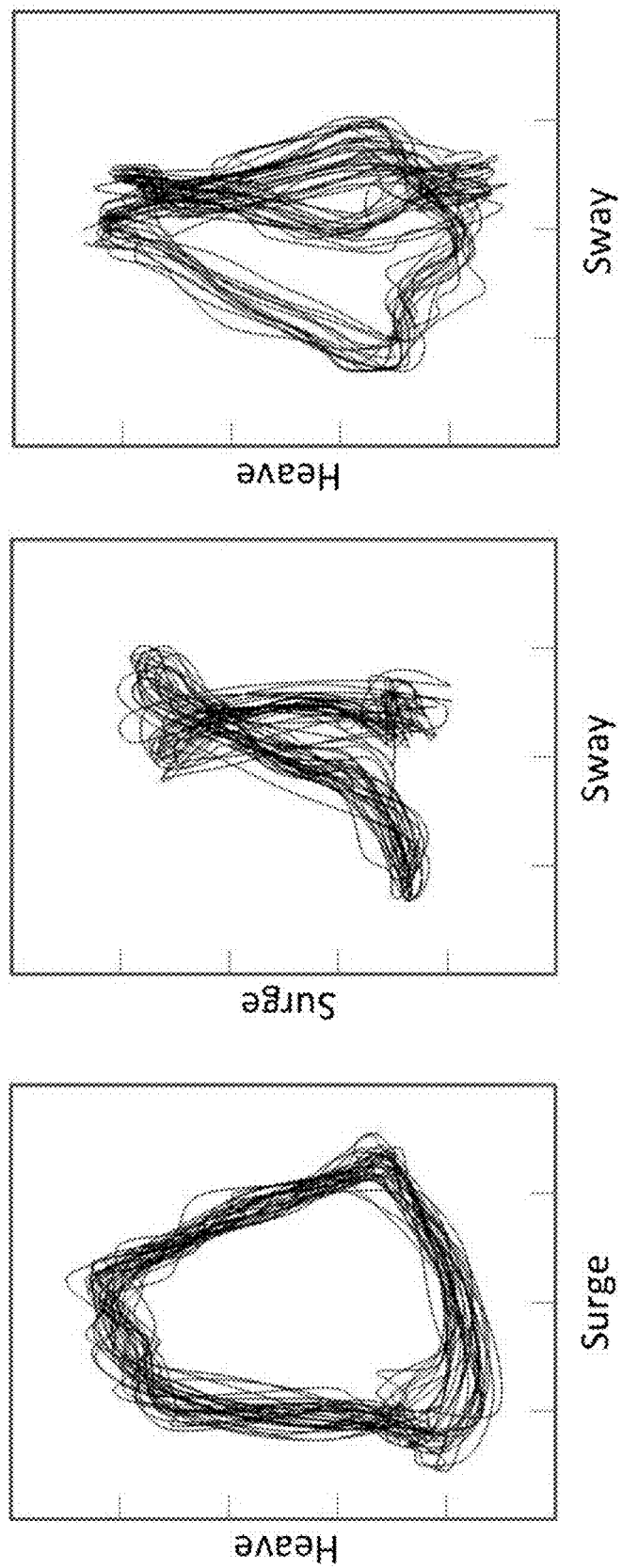
FIG. 13 shows 2D WHLS patterns measured for a dog by placing the accelerometer embedded in a smartphone on its back.

This invention can also be applied to measure the gait for animals. FIG. 13 shows 2D WHLS patterns measured for a dog by placing the accelerometer embedded smartphone on its back. The dog was running on a treadmill at 5.6 km/hr which is much faster than the 2 km/hr speed for human in the WHLS measurement. Due to the anatomic and kinesthetic difference, there are some unique features. First, the sway frequency of a dog is half of the heave and surge frequency, while for human, the frequency of all three movements is the same. Second, the "split fork" pattern seen in many human WHLS's in the Heave/Sway components shows up in dog's gait in the Surge/Sway components. In this particular case, the measurements clearly show that the dog's gait is highly asymmetric and favors toward the right side. Third, the side view of WHLS, or the surge/heave component, shows remarkable consistency with very little variation from stride to stride over a long period of time. The shape is smooth without irregular features found in many human WHLS. This is the most desirable running WHLS. This measurement suggests the usefulness of the invention to measure animal's gait. Applications can be found in selecting and training race horses. This invention can also used by veterinarians in diagnosing kinesthetic problems for sick animals who cannot communicate with verbally.

The present invention has many embodiments of different applications, such as:

To monitor and improve running form for people at all athletic levels with real time monitoring and instruction via Wi-Fi.

To monitor progress of patients in physical rehab program quantitatively with digital and graphical presentation.

To monitor the physical well being of patients suffering from conditions that can impede the movement.

To monitor the gait of physically handicapped patients and improve prosthetic design.

To record digital evidence for sobriety test.

To provide a quantitative measure of back pain or pain in other joints from the slope of the loading rate during the start of surge motion in each step and the correlating acceleration in other components as well as the gait energy associated with such motions. This can be used as a reference to differentiate "fake" physical pain from the real physical pain.

To improve jogging/walking form in real time via a portable device by recording the gait, analyzing the result, pointing out the areas for improvement and giving instructions.

Wearing a portable device (e.g. smart phone with 3 axes accelerometer) on the lower back of the runner (i.e. Center of Mass) to collect acceleration data and running form while exercising.

To calculate the WHLS (Walking, Heaving and Lateral movement Signature) in real time.

To compare the measured WHLS to ideal WHLS and find discrepancy and instruct to make gait correction in real time.

From existing database for ideal running form, to determine the solution to correct this discrepancy.

To give an audio command to the runner to correct his/her running form.

To provide scientific bases for the selecting thoroughbred race horse.

Record and use as biometric identification.

Design of new footwear.

Design of new backpacks and other forms of luggage.

To design exercise equipment that will yield the highest efficiency and least damage to body.

To develop software package so it can be used as a stand-alone gait monitoring with just a hand held device.

To help customer to select the best fitting and most comfortable footwear.

To facilitate veterinarians to pinpoint kinesthetic problems for animals despite that the absence of verbal communication between the patient and the doctor.

A further embodiment of the present invention provides an improvement to any portable gait analyzer with multiple applications using the current concept of gait energy, gait force and gait force image. The performance of the gait analyzer can be further improved by three new algorithms for data analysis. These new algorithms are:

A method to determine the precise timing of key gait events such as Heel Strike and Toe-Push to provide reference points for diagnosing the detailed gait information from the raw data.

A method to convert the acceleration data in all directions to a single power spectrum in time domain known as a Gait Force Spectrum. It provides critical information in terms of the time, direction and magnitude of energy flow during various stages of a gait cycle and the energy partition among components in different directions.

A method to express the phase and magnitude relationship between forward and the vertical acceleration during one step in a form known as Gait Force Wheel. It has unique shape for each individual and reflects the coordination and energy transfer efficiency.

Together, they form a powerful tool set for gait analysis with high temporal and spatial resolution. It can be used for diagnosing gait impairment, assessing the effectiveness of therapeutic and rehabilitation treatment, identifying special medical conditions, sports medicine, athletic performance assessment and training, footwear and backpack design as well as for biometric security authentication.

Gait analysis is the bio-mechanic study of body movements including walking, running, and other physical activities. Traditional gait study employs sequential image capture with cinematographic equipment in the early 1930's and the level of complexity grows to track the trajectories of multiple markers with higher image capturing rate and augmented with other tools such as force plates as the technology advances. Despite the increasing complexity, this approach still faces two major short-comings. One involves the bulkiness and confinement of the set-up and the lengthy analysis time that severely limit its value as a routine clinical tool. Another fundamental limitation is the gap between the measured data in displacement and the useful data in acceleration which is more directly tied to bio-mechanic analysis. The transformation of displacement to acceleration involves a double integration operation that will smear out the fine features. To compensate for this discrepancy, traditional gait analysis is often augmented with simultaneous measurements with other monitoring devices such as force plates at the expense of further increasing the system complexity.

This problem can be alleviated by using a 3-axes accelerometer (i.e. Inertial Measurement Unit or IMU) placed near the Center of Gravity (COG) on the body to directly measure the acceleration during physical movement. This approach not only reduces the size and complexity but also provide more direct information on bio-mechanical details. However, most of the works are focused on the cadence or with IMU placed on other parts of the body, the analysis and measurement are different from the approach described in this invention.

Figure 14:
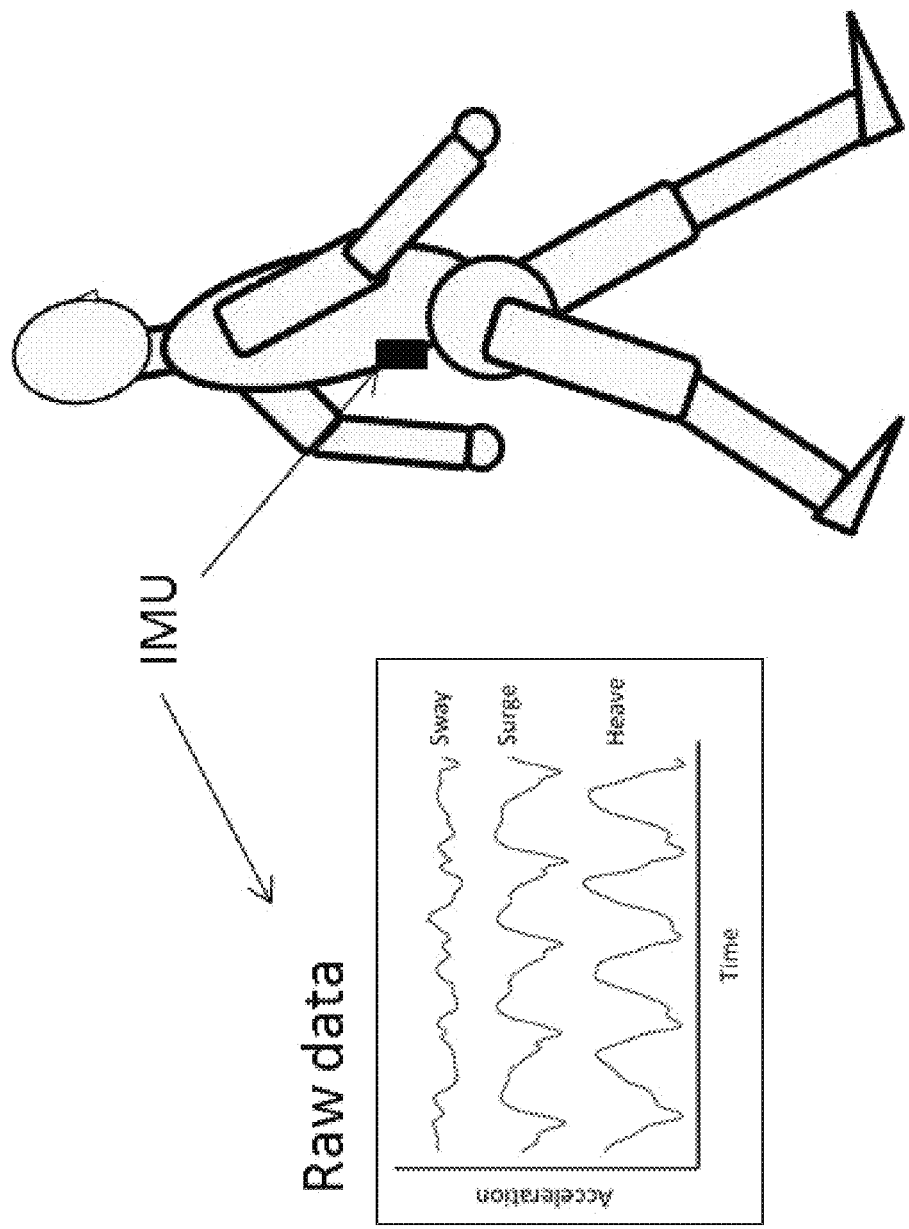
FIG. 14 shows the placement of the IMU during gait analysis.
Figure 15:
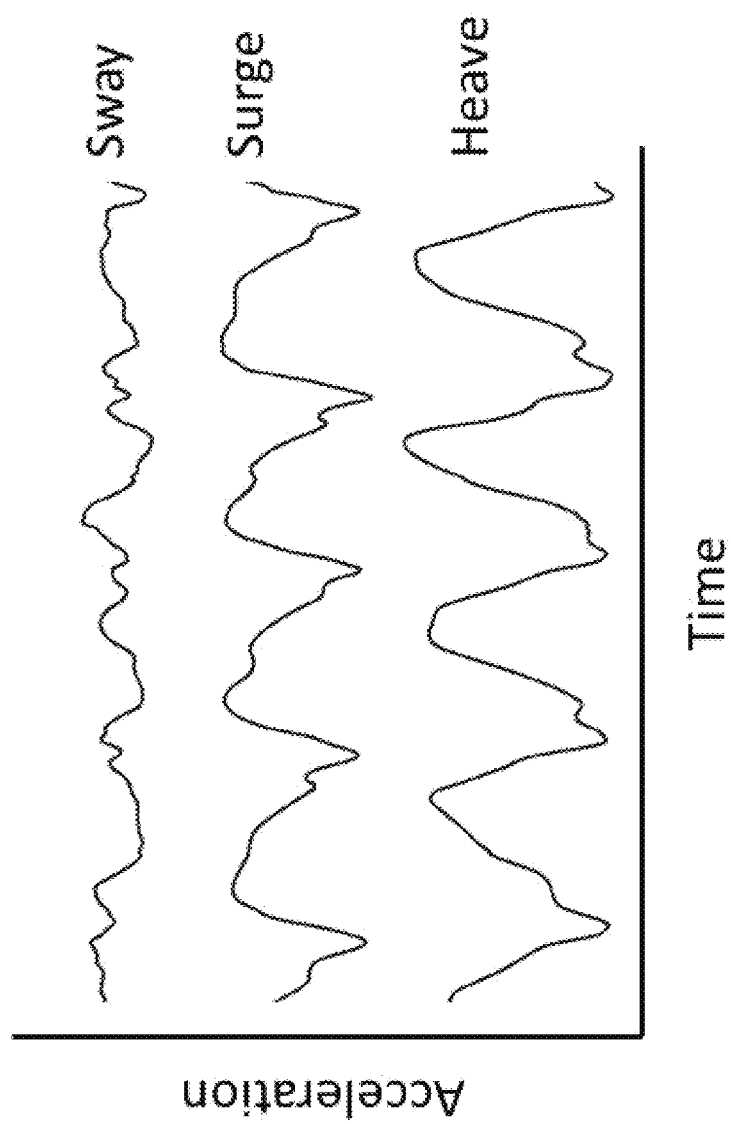
FIG. 15 shows the raw acceleration data of 2 strides collected during a gait measurement.

Description of Different Embodiments of Present Invention:

The hardware and measurement technique have been described previously. Basically, a 3-axes accelerometer (i.e. Inertial Measurement Unit or IMT) is attached tightly against the lower back of the individual being tested as shown in FIG. 14. The location is chosen for its proximity to the center of gravity (COG) of the body where the reaction force from contacting the ground is mostly damped under normal gait condition. Any residual interference from the residual ground reaction force is further removed by applying band pass filter during data acquisition. Consequently, the data only records the acceleration of the COG with the necessary clarity and high signal to noise ratio for in-depth clinical interpretation. FIG. 15 shows the typical data taken for a person walking on flat ground. It consists of three oscillatory acceleration data set in the orthogonal directions: up and down (heave or vertical), side to side (sway or horizontal) and forward and reverse (Surge or the direction of travel). The corresponding anatomical terms for these directions are: superior/Inferior; medial/lateral and anterior/posterior, respectively. This invention describes three algorithms that can be used to extract useful clinical information from the raw data. The data rate used in this invention is 100 Hz. With the IMU sensitivity of 0.003 g, where g is the gravitation constant of 9.8 m/S$^2$, the displacement sensitivity at 10 Hz is only 0.1 mm thus making the detection of very minute change in COG possible. It should also be pointed out that the present set-up only measures the linear motion in three axes. Rotations about the three axes including pitch, roll and yaw are ignored. It proofs for normal walking, the data prove to be adequate. However, for more detailed analysis, a gyro should be used concurrently with the IMU to record all six degrees of freedom including both translation and rotation. The analysis algorithm will remain the same except the acceleration vectors will be determined by taking rotations into account and carrying our appropriate mathematical transformation. Each of the aforementioned three algorithms can be performed by a computer or a computing device having one or more processors. The computing device can be a mobile computing device such as a smartphone.

Figure 16:
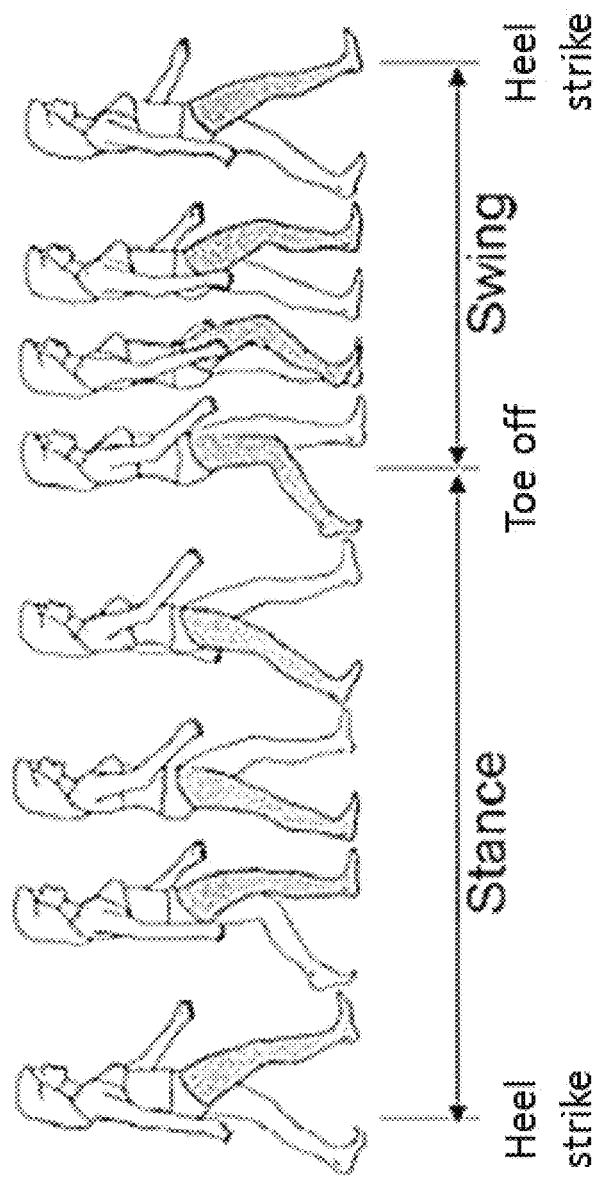
FIG. 16 shows the graphical representation of a normal gait cycle.

Gait Cycle Algorithm—the Identification and Timing Determination of Key Gait Events In one embodiment of the present invention, there is provided a gait cycle consists of one stride or two steps with key events shown in FIG. 16. Each step starts with a heel strike and is followed by a stance phase and a swing phase while the same phase sequence of the other foot is in the reverse order. Stance Phase describes the sequence when the landing foot remains on ground and push backwards until toe-push to start the swing phase. The duration of this phase is approximate 62% of a stride for a normal human person. This algorithm describes a method to time mark two key events: the Heel Strike (HS) and the time that happens just before toe-off.

Figure 17:
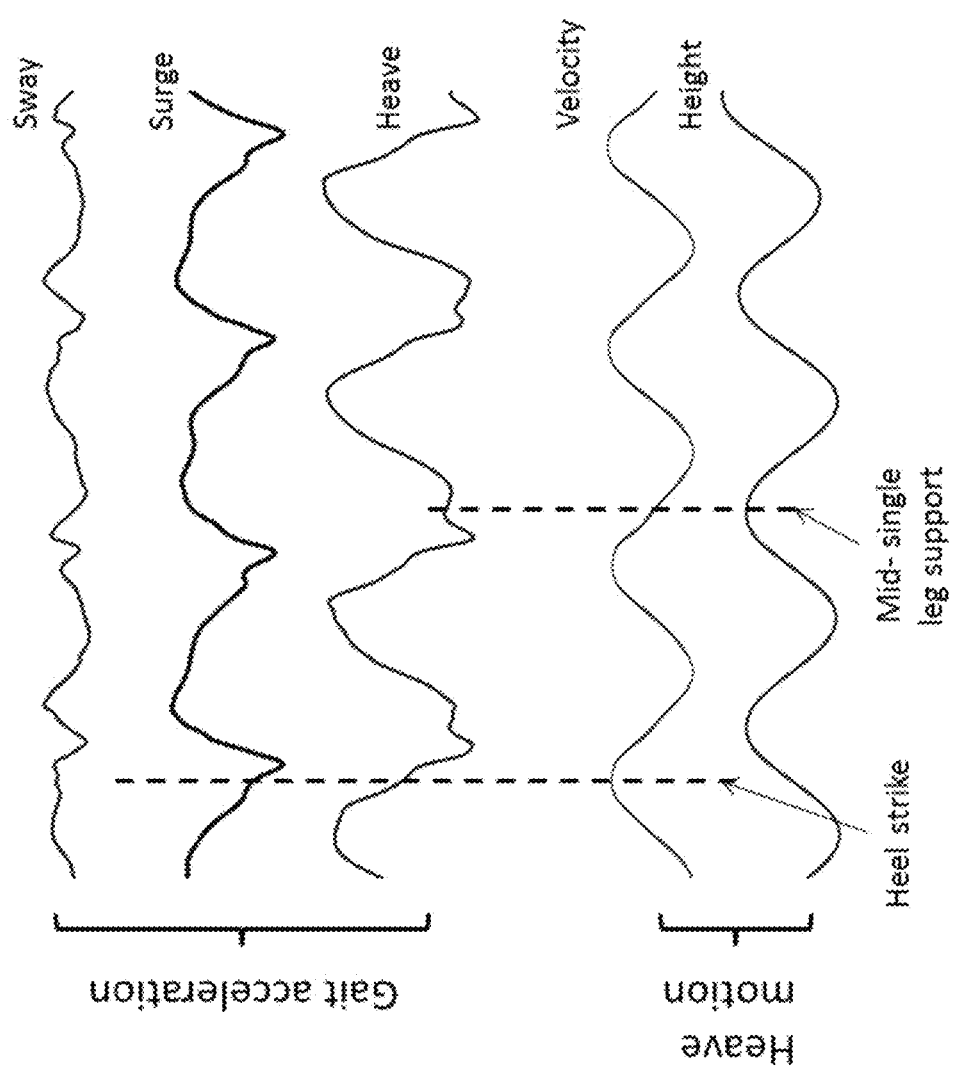
FIG. 17 shows the determination of the timing of heel strike and mid-single leg support from raw acceleration data.

First, the inventor focuses on the acceleration data in vertical direction. After toe-off from one foot, the COG of the subject will ascend and move forward. As the forward energy is being consumed, the COG starts to descend and the downward velocity increases until it reaches maximum when heel strike of the other foot occurs. The situation is similar to the description of the trajectory of a free falling object when it hits the ground at maximum velocity according to Newtonian Laws of motion. This timing can be determined accurately by converting the raw acceleration data in the vertical direction (i.e. Heave) to velocity by an integration operation. An example is shown in FIG. 17 that depicts the precise time of heel strike to start a gait cycle.

The second key gait event is the toe off of the opposite foot. Just prior to it, the height of COG is at the lowest. Therefore, its time mark can be determined from the minimum height of COG in the gait cycle by a double integration of the acceleration data as shown in FIG. 17. It is well known that for normal gait, the time duration between these two events, or the stance phase, amounts to approximate 62% of each gait cycle. Agreement found in over 100 human subjects offers further validation to this approach.

Gait Force Spectrum Algorithm—Estimation of the Gait Force Spectrum

Figure 18:
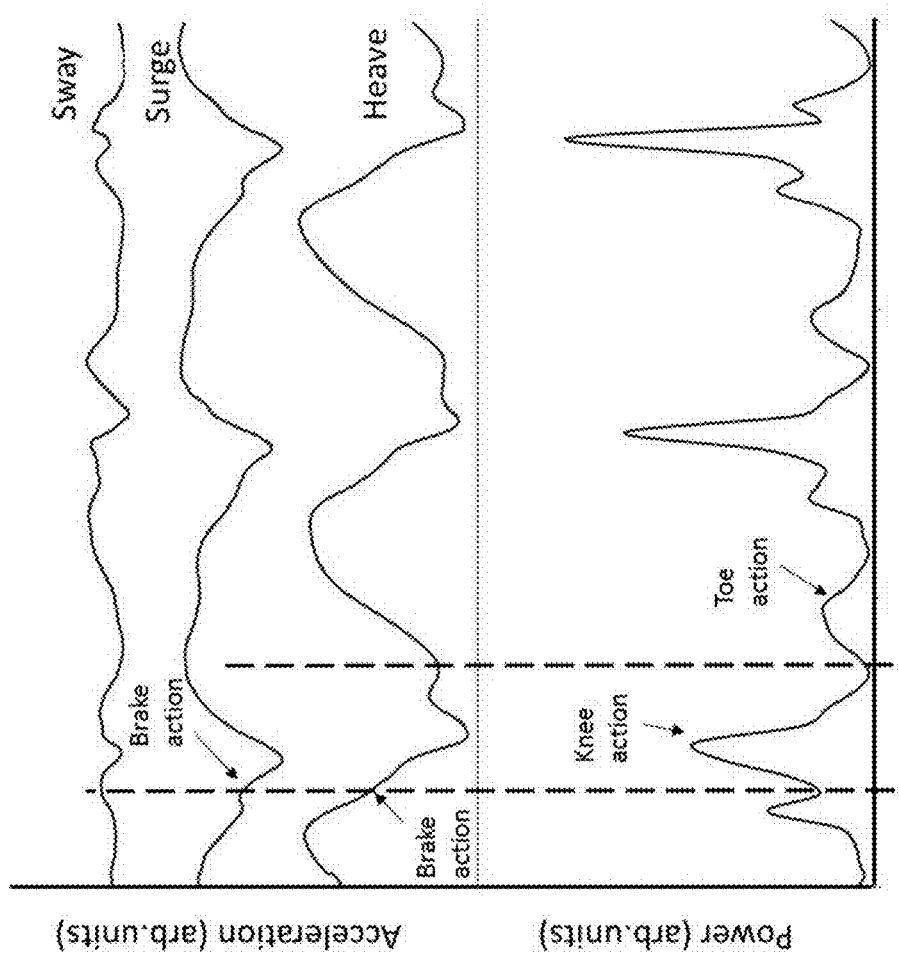
FIG. 18 shows the Gait Force Spectrum of one normal stride.

In another embodiment of the present invention, there is provided a Gait Force Spectrum as a new concept and a powerful gait analysis algorithm that converts the acceleration data in all directions to a time dependent power spectrum. Its formulation is based on the Gait Force concept disclosed in U.S. Non-Provisional patent application Ser. No. 14/622,933, cited above, by calculating the Dynamic Instability Index (DII) or Gait Power value at each time and expressing the results as a time dependent spectrum. The horizontal axis represents time and the vertical axis represents power. Therefore, for any time variation of DII, the area under the curve within a time interval represents the energy. FIG. 18 depicts a gait force spectrum for the measurement shown in FIG. 17. The peaks are interpreted as alternating energy injection and rejections channels, or simply as the "acceleration" and "deceleration" actions in forward direction, "move up" and "move down" in vertical direction or "move to left" and "move to right" in the side oscillatory motion. Their magnitude, timing, duration and the direction of energy flow offer quantitative information about the gait.

Heel Strike, determined from the first algorithm, occurs precisely at the onset of a large peak labeled "A" in the Gait Force Spectrum. It signals the start of injection of energy produced from the subsequent knee action. This peak is followed by a second peak which represents the energy outflow as the COG is descending and the forward movement is slowing down. For a normal gait, this peak is small and sometimes only appears as a shoulder buried by the dominant energy injection peak "A". The next well-defined peak "B" is broad but with smaller magnitude. It corresponds to the energy injection process from the toe-off action of the opposite foot. For a healthy gait, the area ratio of the two peaks is approximately 2:1. However, for a person with flat foot condition, this second peak is extremely small or even non-existent. The ratio of the two peaks offers a quantitative assessment of impairment condition. The opposite extreme is tip-toed walking where the second peak due to toe-off is more dominant.

Figure 19:
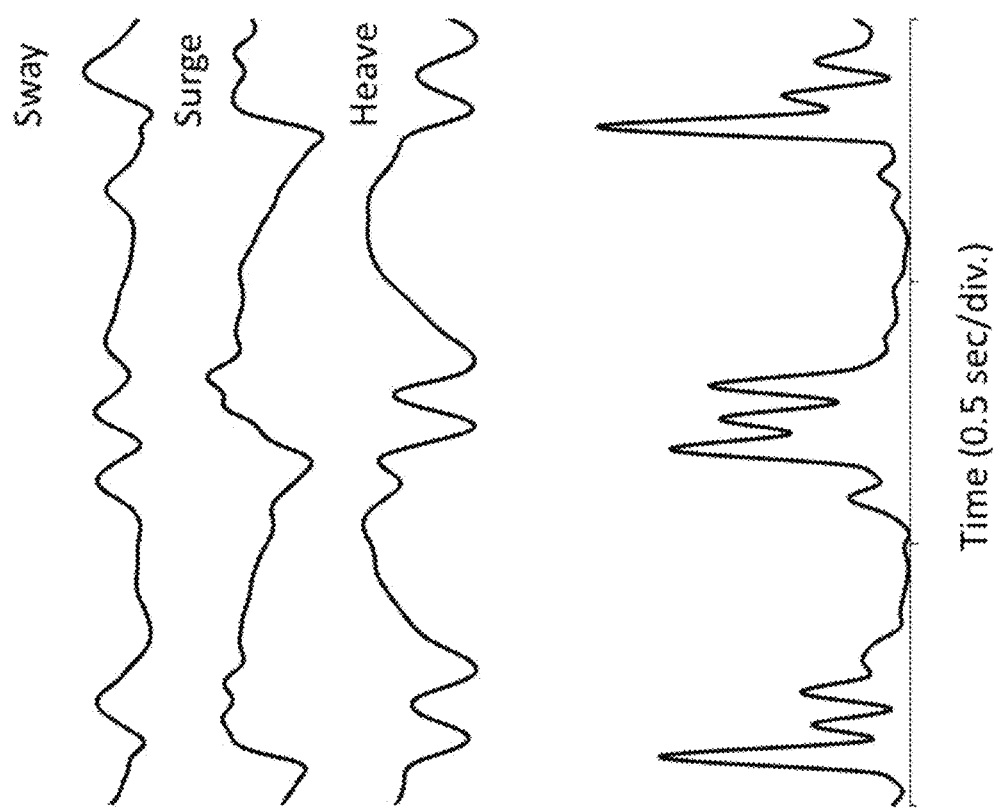
FIG. 19 shows the example of a poor Gait Force Spectrum with multiple spiky peaks.

The normal Gait Force Spectrum which is a series of repeatable peaks with clear distinction among the energy injection and rejection actions. For a person with gait impairment conditions, the Gait Force Spectrum has irregular and sharp peaks reflecting the discomfort level due to the symptom. An example is shown in FIG. 19. Such features can be used to identify different gait impairment conditions and assess the effectiveness of treatment.

Gait Force Wheel Algorithm—Generation of the Gait Force Wheel

Figure 20A:
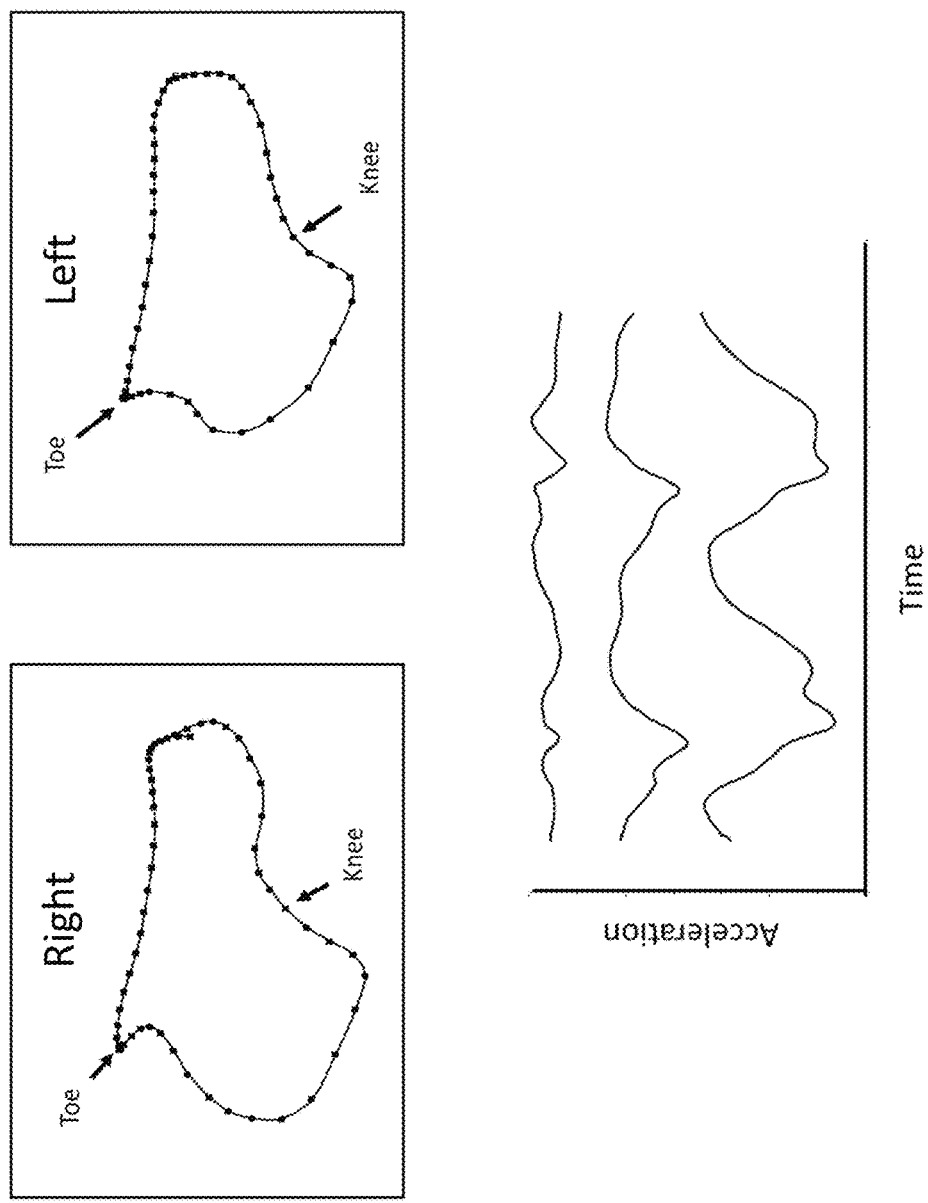
FIG. 20a shows the Gait Wheel and Gait Pattern of a subject A. Subject A's phase difference between two energy injection channels is close to 180 degrees.
Figure 20B:
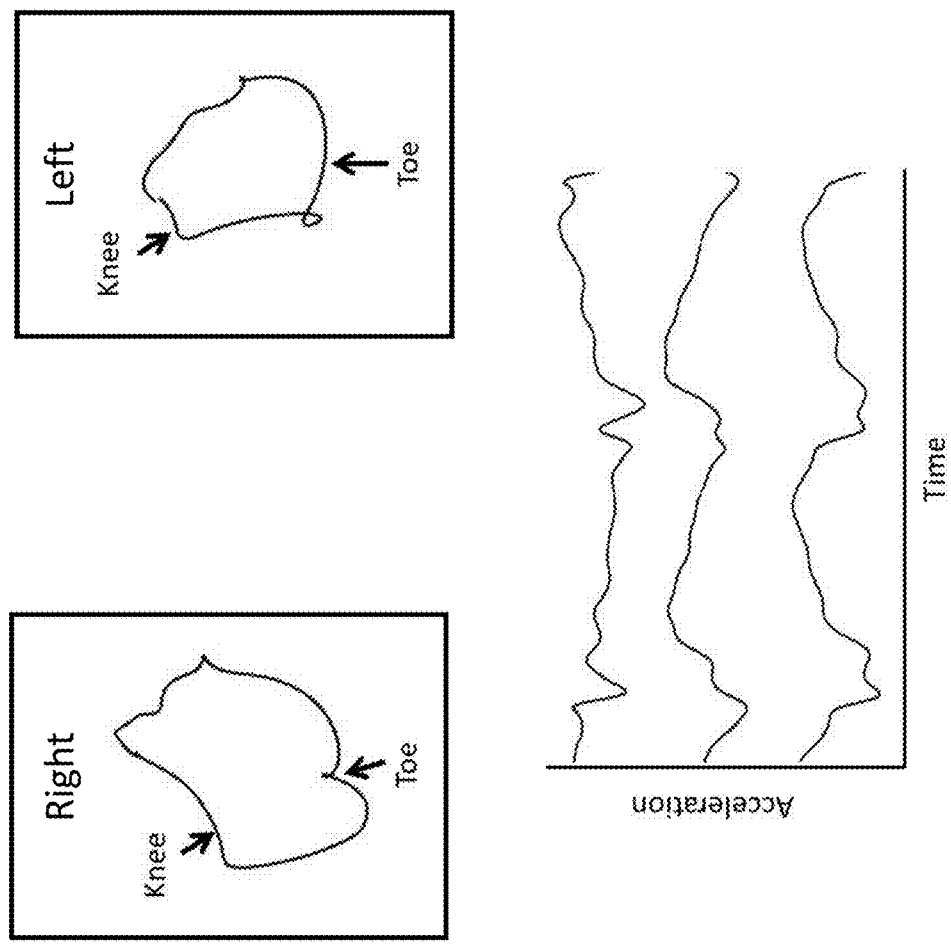
FIG. 20b shows the Gait Wheel and Gait Pattern of a subject B. Subject B's phase difference between two energy injection channels is only about 120 degrees therefore less efficient.

In yet another embodiment of the present invention, there is provided a Gait Force Wheel as another useful algorithm to extract gait information from the measured data. It uses a graphic representation to reflect the phase relationship between the accelerations along two different orientations. The most useful set is between surge (forward) and heave (vertical) movements. It can be regarded as a measure of coordination and the timing of energy flow within a gait cycle. In this practice, a gait force wheel is depicted by plotting the magnitude of forward acceleration (surge) vs. vertical acceleration (heave) as shown in FIG. 20a and FIG.

20b for two test subjects. The timing of energy injection from knee and toe actions are determined from Gait Force Spectrum and the shape, symmetry and the timing of energy injection point into the Gait Force Wheel in the abstract acceleration space can reveal more information about gait quality. Subject A has a better gait pattern with very similar gait force wheel for left and right steps. The injection times from two energy sources are nearly 180 degrees in phase which is the most efficient arrangement akin to the timing of a two cylinder engine. For subject B, the two gait force wheels are vastly different, and the phase difference between two energy injection points only 120 degrees which is far from the ideal condition of 180 degrees thus the energy usage is less efficient.

Assignment and Diagnose of Gait Events

With these three algorithms in place to identify the timing of key events, and the knowledge of the energy flow in and out of the gait in high time resolution, detailed bio-mechanic analysis of the gait can be used both as a clinical and a research tool. Here are some examples of both healthy gait and those with gait impairment conditions:

Case 1—Normal Gait

Figure 21:
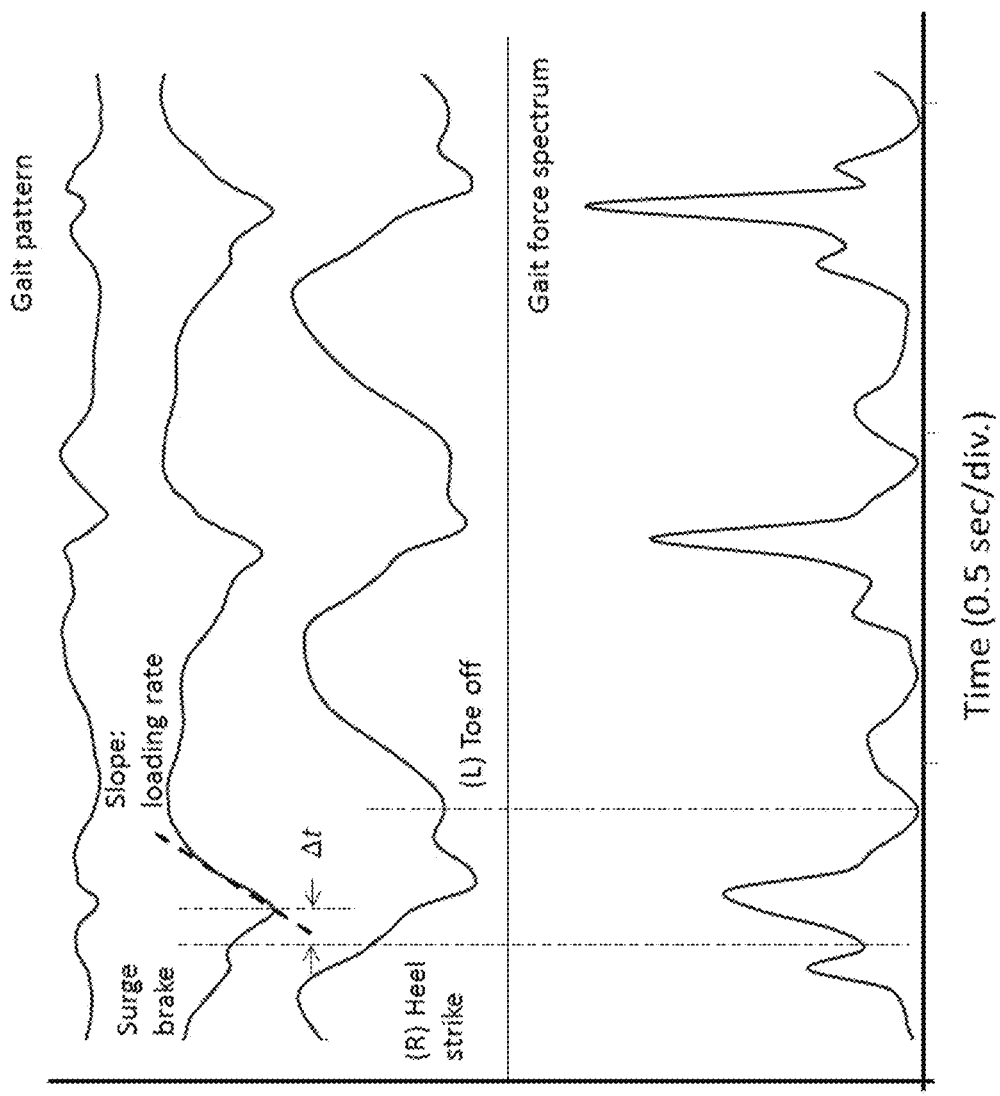
FIG. 21 shows the Gait Force Spectrum analysis of heel strike in a normal gait.

After data acquisition and time marking the key events, detailed analysis can be carried out for each movement as the gait cycle unfolds. FIG. 21 depicts the bio-mechanic information of key events in one normal gait cycle.

Heel Strike (Initial Ground Contact):

The precise timing of heel strike is first determined by the first algorithm described in the previous section. Heel strike triggers a sudden decrease in acceleration in all three directions. In the vertical direction, it changes the slope due to knee bending. In the forward motion or surge, heel strike acts like a "brake" to cause a sudden slow down. In the sway (side to side) motion, heel strike starts with a movement either toward the right (i.e. positive acceleration) or left (negative acceleration). This trend can be used to label whether the heel striking foot is right or left.

Knee Bending and Extension (Loading Response):

After initial heel strike, the knee of the landing foot will immediately bend to serve two purposes: (1) Absorbing the shock of the ground reaction force to reduce injury to the joints and the back; (2) Loading energy which will be released during the stance phase to propel the body forward. This action is reflected in the change of slope of the downward acceleration. In addition, during a normal gait, the knee bending and loading phase is followed by knee extension, also known as loading response, to inject energy into the gait cycle. This sequence results an S-shaped behavior with a well-defined inflection point in the downward acceleration change of the COG. The absence of this feature indicates the lack of proper knee bending.

Forward Acceleration:

Immediately after heel strike and knee bending, energy is injected from knee extension (or the loading response) into the gait cycle to propel motion forward. The ascending slope of the surge acceleration increase is a measure of "explosiveness" or "loading rate" referred by force plate based measurements. It can be used to assess individual's physical wellbeing and the correlation of this quantity to one's age as well as fitness is found. For example, severe back pain or other discomfort can contribute to weak loading rate. At the same time, it can also lead to lower sustainability of surge acceleration. Therefore, the change of these features can be used to monitor a person's pain level or the lack of it. Another important parameter is the time lag, $\Delta t$, between the heel strike and the onset of forward acceleration. The delay time depends on each individual and can be used as a diagnostic parameter.

Figure 22:
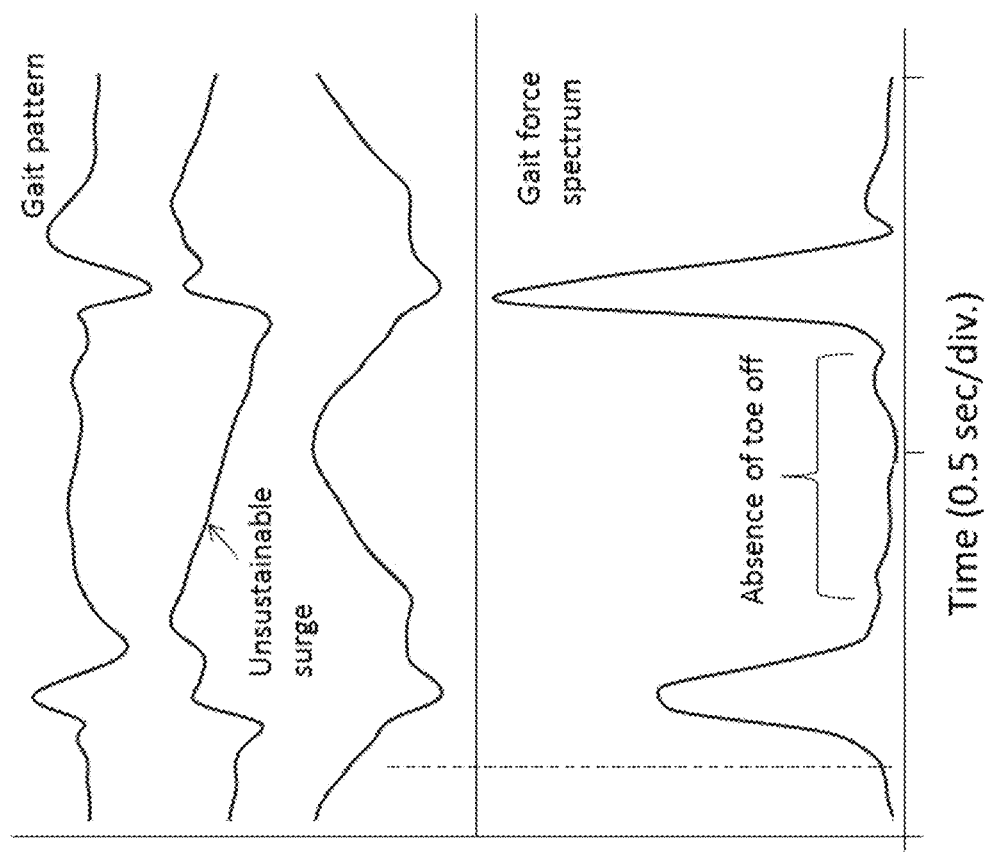
FIG. 22 shows the Gait Force Spectrum analysis of Flat Foot condition.

Heel-Toe Action:

After the loading response stage, the heel of the landing foot will exert a downward force to the ground. Consequently, a ground reaction force is produced to move the person. A portion of the ground reaction force is used to push the body sideward to the other direction. This action can be seen in the change of sway acceleration. A few milliseconds later, the toe push from the other foot takes place. This motion will push the body toward the direction of the landing foot. This sequence of zigzag movements produces a double minima in the heave acceleration. Also worth noting is the time alignment between the minima in the heave acceleration and the change of acceleration direction in the sway motion during this sequence of events in a normal gait. However, gait impairment conditions can cause time misalignment so the minima do not correspond precisely to the change of sway acceleration. This piece of information can be used for gait diagnosis. In some medical conditions such as Flat Foot, the gait does not have a quality toe-off action to provide the extra energy to sustain forward acceleration. In that case, after reaching the peak at a larger than average loading rate, the forward acceleration decreases monotonically as shown in FIG. 22. The feature is also reflected in its gait fore spectrum.

Figure 23:
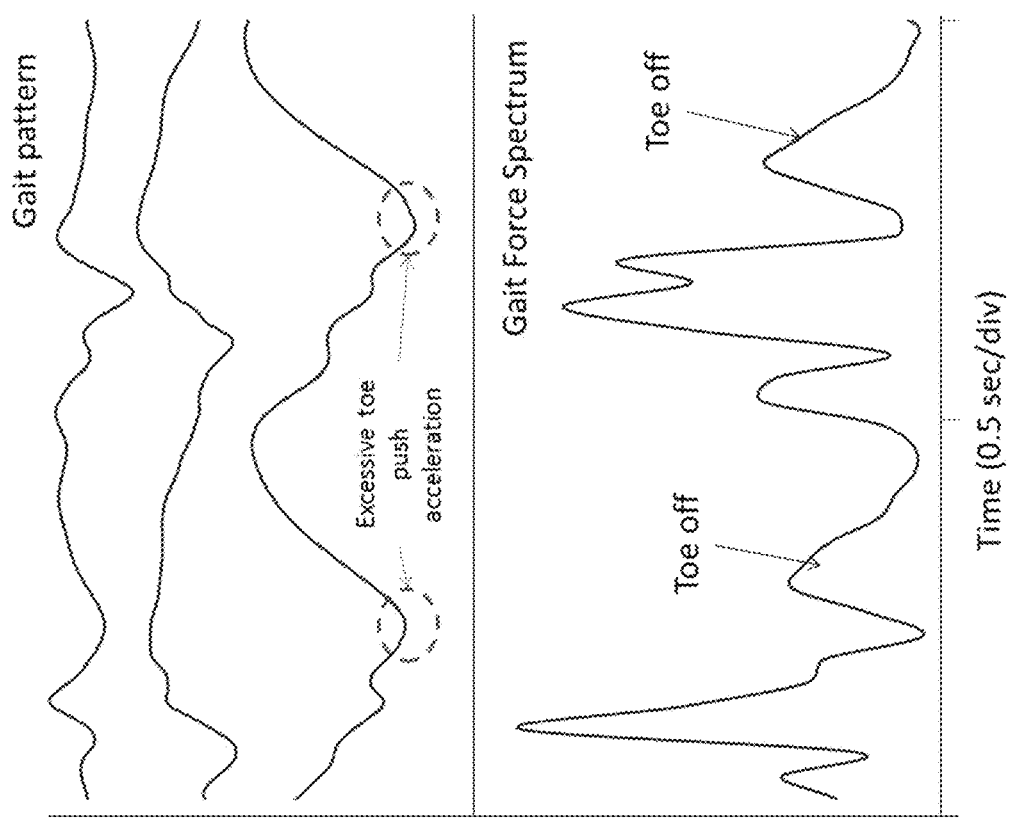
FIG. 23 shows the Gait Force Spectrum analysis of Tip-toe walking.

Opposite to flat foot condition which exhibits little of no toe push, tip-toed walking is also a gait impairment condition. Its characteristic heel-toe action can be easily detected. Due to excessive toe push, the second minimum in the vertical acceleration is dominant and the peak associated with toe off energy injection in the Gait Force Spectrum has magnitude much greater than normal. Example is shown in FIG. 23.

Case 2—Special Gait Features

Figure 24:
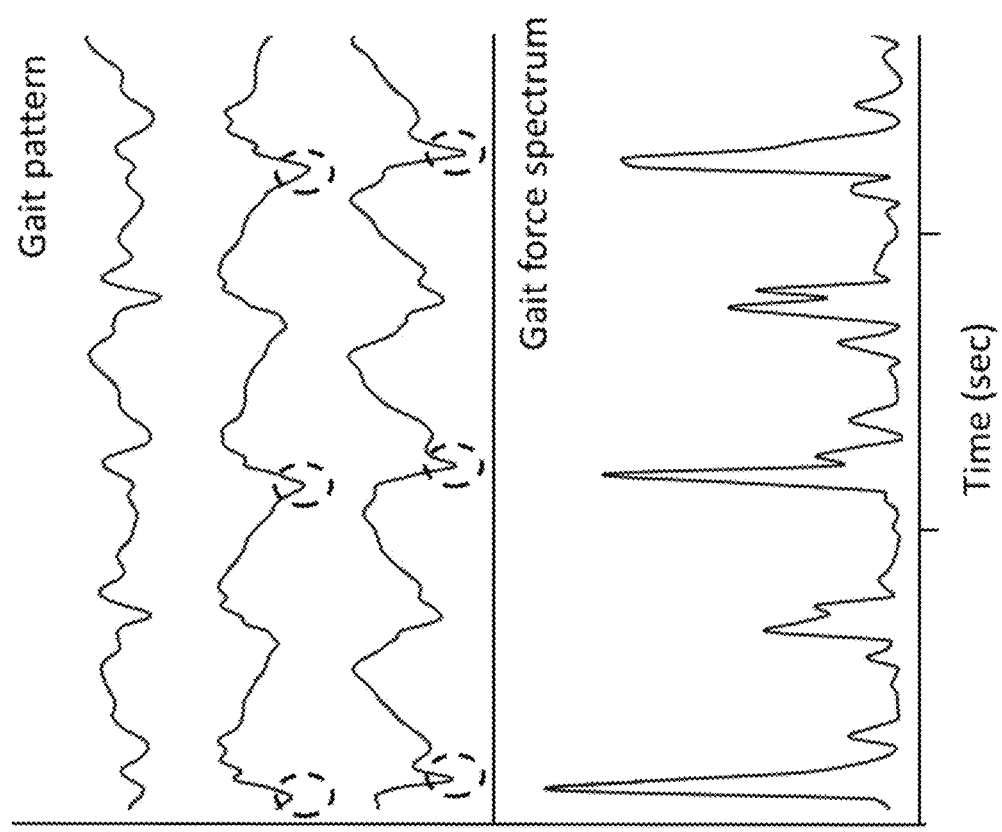
FIG. 24 shows the Gait analysis of an individual with Leg Length Discrepancy Syndrome.
Figure 25:
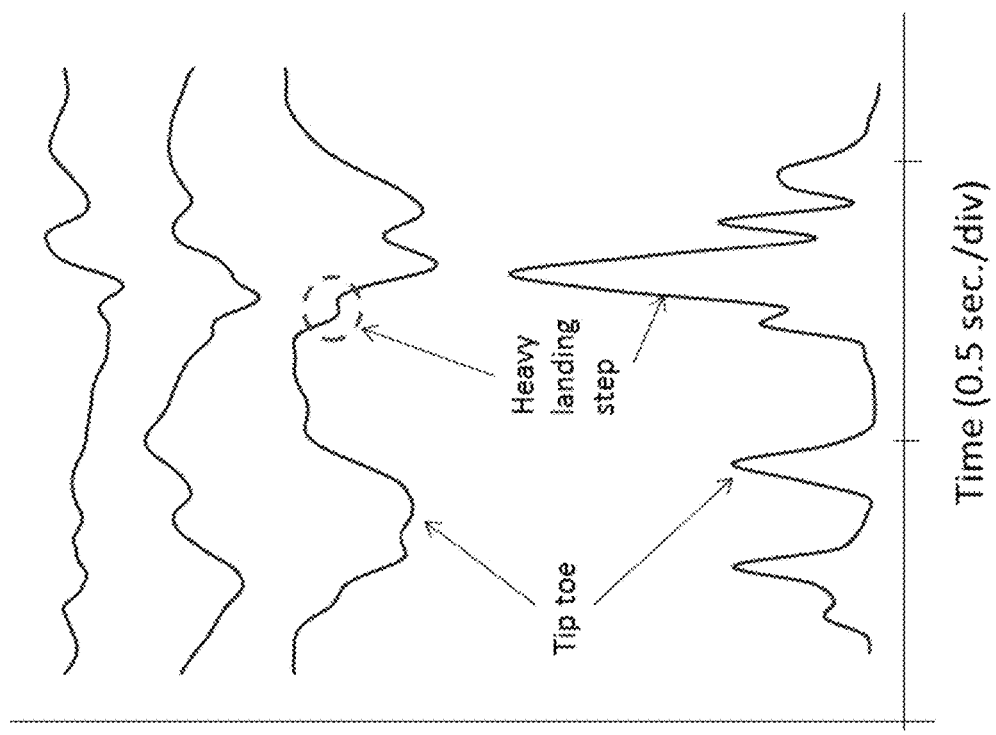
FIG. 25 shows the Gait force signature of excess heavy footing.

This invention can identify special features associated with gait impairment conditions. Some examples are:

Alternating Acceleration Magnitude:

In some cases, the vertical, forward and sideward accelerations, either independently or acting as a whole, show distinctive alternate magnitude variation, an indication of one foot hitting the ground harder than the other or one step advancing faster than the other, or asymmetric sway to one side, or all of them happening in unison. An example is shown in FIG. 24 in which the downward acceleration for the left step is greater than that of the right step. This abnormal feature is often accompanied by the lack of proper knee bend in the corresponding leg that shows up as the absence of S-shaped change of downward acceleration. One possible attribution is the Leg Length Discrepancy Syndrome (LLD), a medical condition in which the shorter leg tends to land with greater force with a straight knee. An example of the Gait analysis of an individual with Leg Length Discrepancy Syndrome is shown in FIG. 24. In extreme case, the heavy landing can result excessive ground reaction force which is detectable as a positive blip at the moment of heel strike shown in FIG. 25. All these features can be used as a preliminary screening of the LLD condition for further diagnosis. With large clinical population and data base correlation, it is possible to use this information to estimate LLD severity quantitatively.

Figure 26:
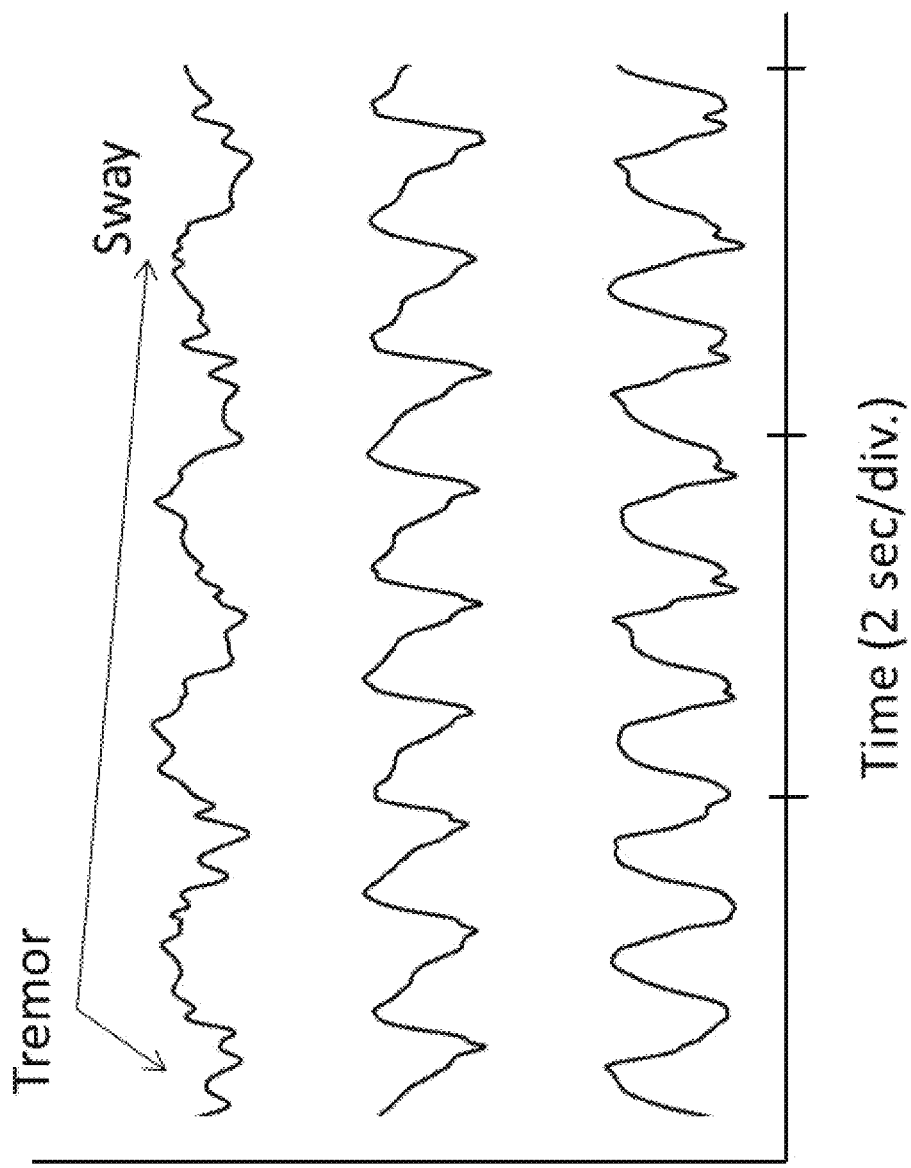
FIG. 26 shows examples of knee tremor due to weak knees. The unique feature shows up as the high frequency oscillation in the sway acceleration.

Knee Tremor:

Weak knees cause tremor in the side to side movement. With the high sensitivity of this method, this condition can be detected in the form of high frequency oscillation in the sway acceleration. An example of a normal gait and a gait of a person with weak knees is shown in FIG. 26. The weak knee induced tremor is approximate 8 Hz in this case.

Figure 27:
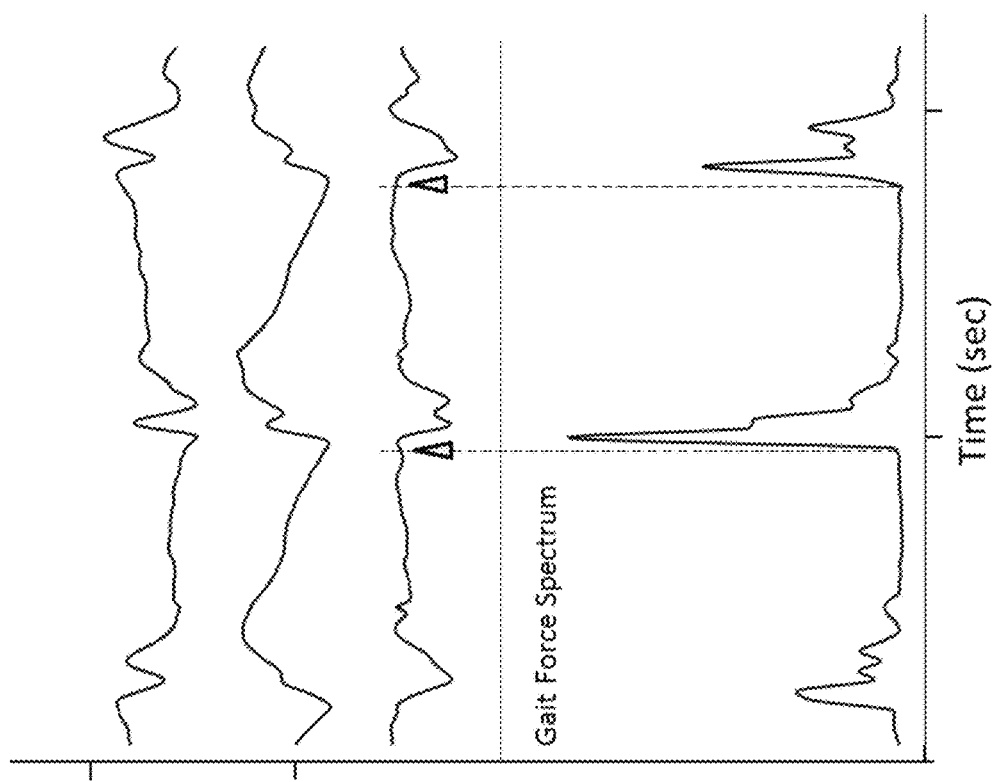
FIG. 27 shows the Gait signature of high knee lift and flat placement of the foot on the ground without proper heel strike. Heel strike timing is marked by the symbol "Δ" which is also the onset of the large peak in the gait force spectrum.

High Knee Lift:

Abnormal gait condition such as high knee lift can also be identified with a characteristic signature shown in FIG. 27. In this case, at the start of every step, instead of moving the leg forward with proper heel strike, the knee is lifted and placed down flat on the ground. This behavior is found among patients suffering from severe LLD conditions, back pain and patient with hip and knee pains. Therefore, this simple measurement can be used to diagnose the cause and monitor the recovering progress.

Figure 28:
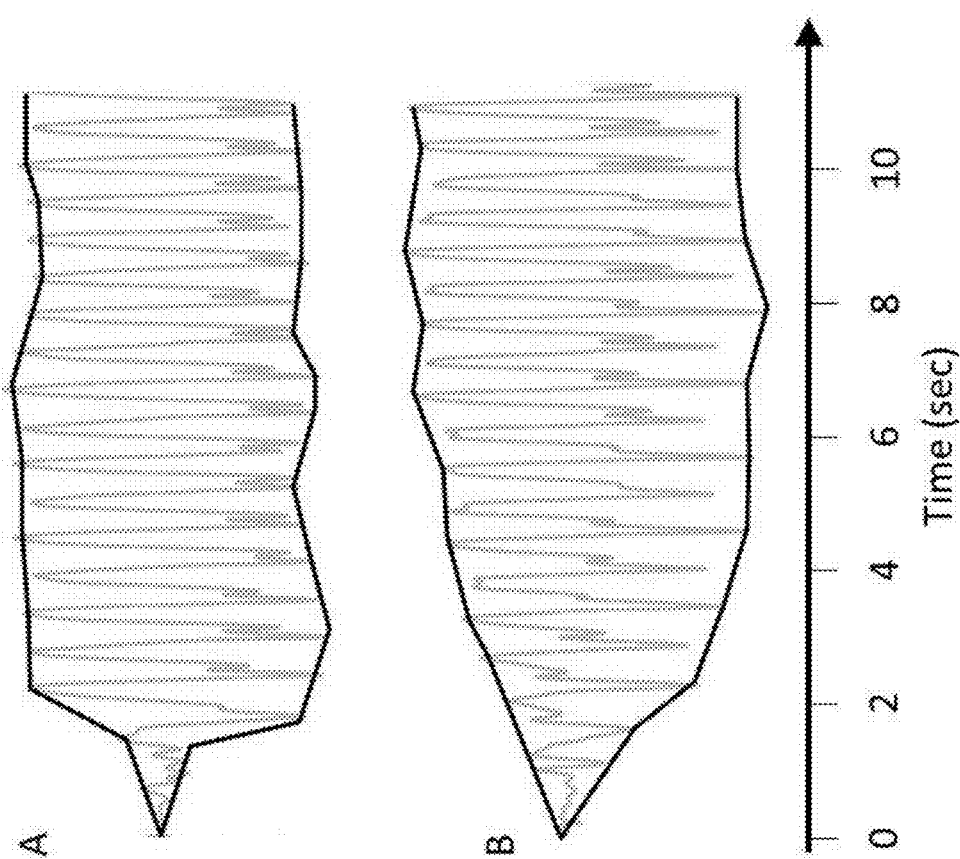
FIG. 28 shows the evolution of the heave acceleration for two individuals with different time to reach steady state. Subject A reaches steady state and comes to complete step from stead in just 2 steps. For subject B, it takes 10 steps to reach the steady state.

The rate of evolution to achieve steady gait:

The rate to achieve a steady gait and the rate to slow down to a completely stop differ for each individual. Two examples are shown in FIG. 28. For individual A, it took only two steps to reach a steady state. However, for individual B, the gait pattern evolves gradually to a steady state in about ten steps. The pattern and time dependence differs for each individual and also contains vital clinical information.

Coordination and Energy Synthesis

Figure 29:
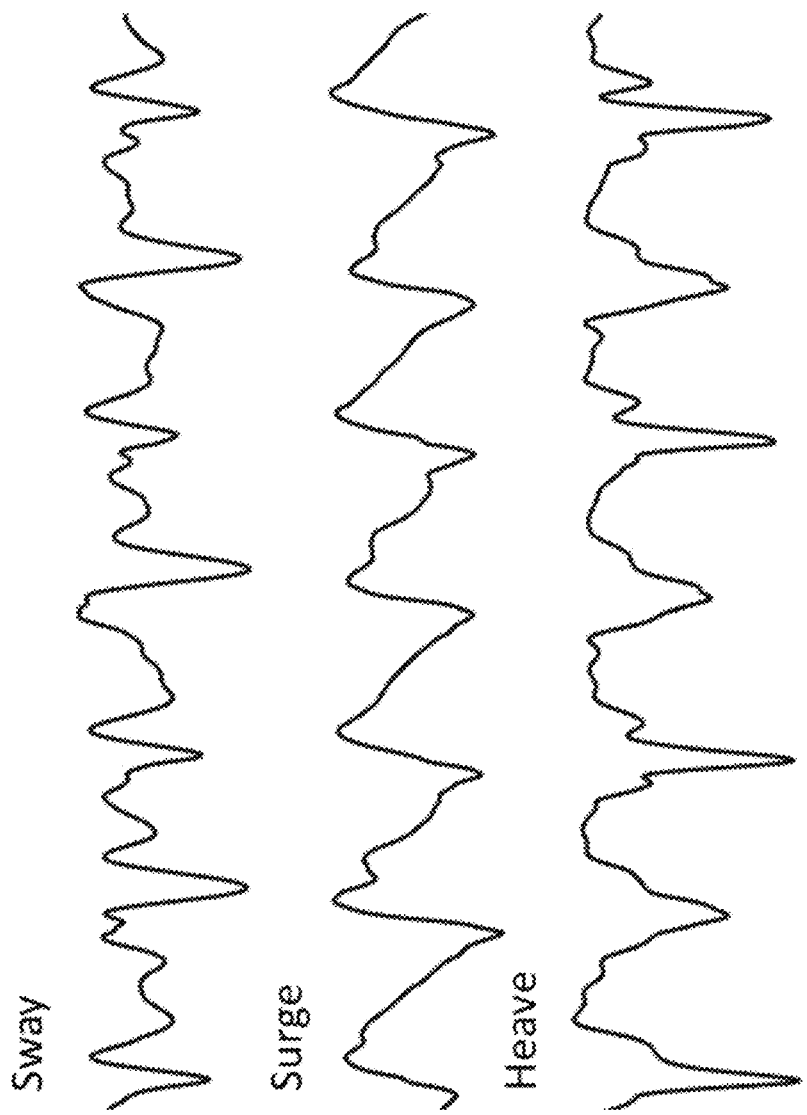
FIG. 29 shows an example of coordination and gait synthesis.

In some cases, despite the major difference in the bio-mechanics of two consecutive steps shown in FIG. 29, their surge acceleration remains nearly the same to maintain a steady movement forward. This feat is attributable to neuro motor controlled coordination by synthesizing the forward movement with discrete segments of injection energy in a timely manner. This invention can be an effective tool to provide clinical information about this complex process.

Hip Replacement Patient

Figure 30:
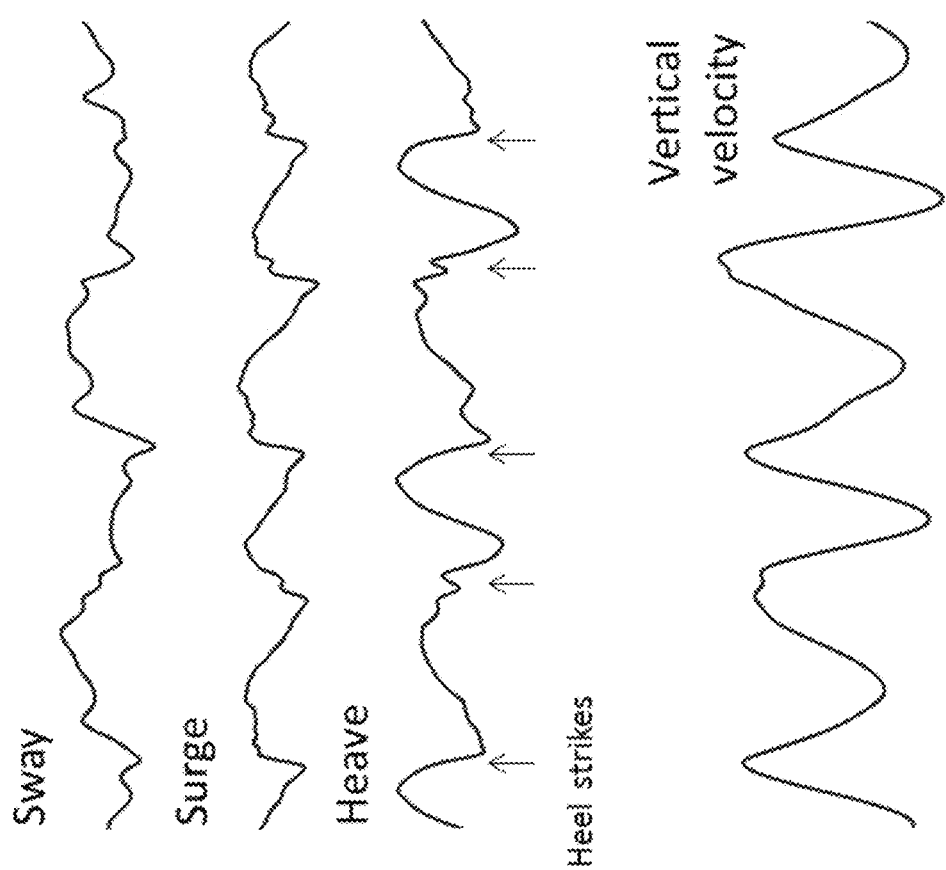
FIG. 30 shows the Gait pattern and gait force spectrum of a hip replacement patient during rehabilitation.

FIG. 30 shows the analysis of a hip replacement patient during rehabilitation process. The data, after analysis with algorithms described in this invention, gives detailed quantitative information about his condition. In addition to the obvious asymmetry between the side that received hip replacement and the other side, there other notable conditions: inconsistent cadence with non-sinusoidal heave velocity, inconsistent heel strike between right and left steps, and complete lack of toe off in both steps and very low overall gait energy. This clinical information can serve as a base to monitor the rehabilitation progress.

Parkinson Disease Patient

Figure 31:
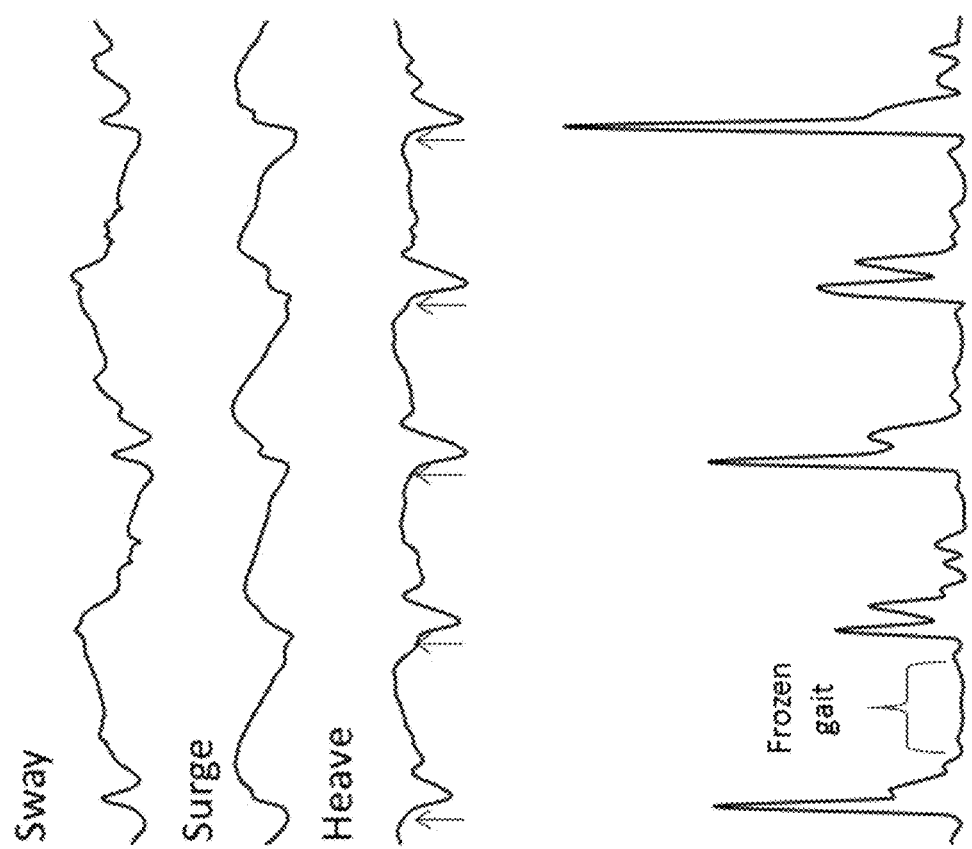
FIG. 31 shows the Gait pattern and gait force spectrum of a Parkinson Disease Patient.

FIG. 31 shows the analysis of a patient suffering from Parkinson Disease. Aside from the well know features such as high knee lift and light footing, the Gait Force Spectrum analysis also distinctively reveals a long duration of inaction in every step which is the characteristic "Frozen Gait" for Parkinson patients. Again, this measurement and analysis provides a quantitative assessment of the patient's condition and valuable information in monitoring treatment and rehabilitation process.

Gait Measurement for Children

Figure 32:
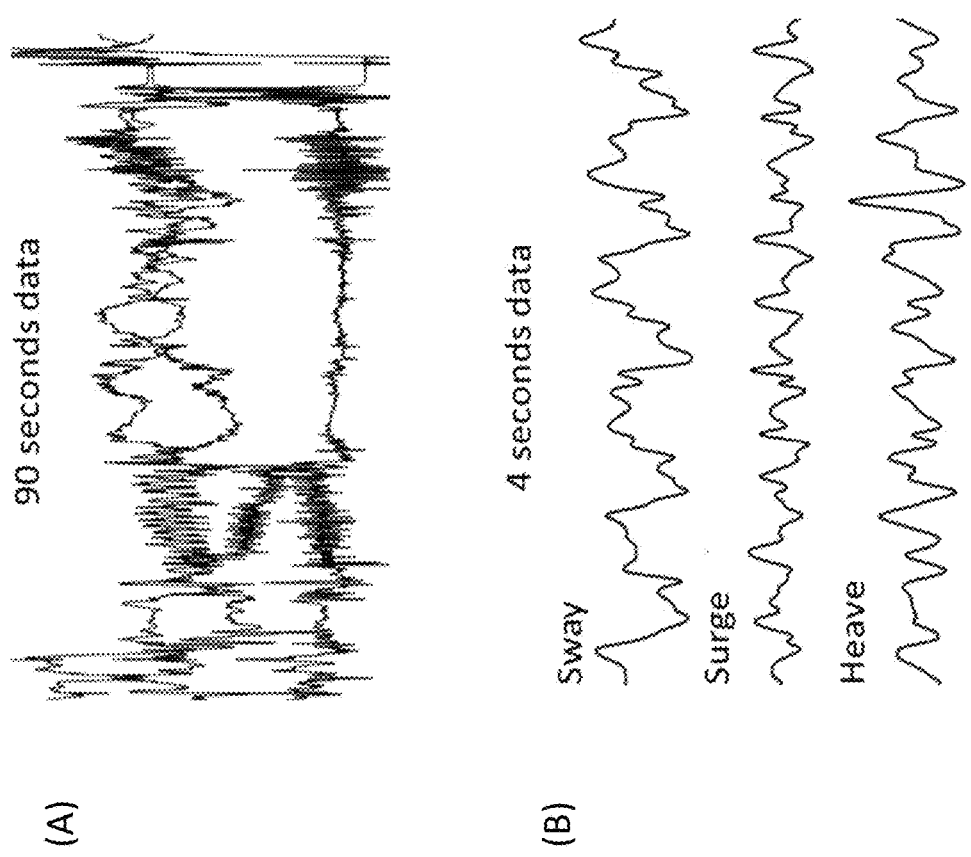
FIG. 32 shows the Gait pattern and gait force spectrum of a 2 year old toddler. (A) Data collection in 90 seconds long span of random activity; (B) Useful gait patter selected and retrieved from the 90 seconds data.

There is a critical need for monitoring the gait for children from toddler to teenagers in order to provide valuable information on physical growth and detect gait impairment at an early stage. However, due to the short concentration span and the difficulty to administer conventional gait analysis to children of young age, such task poses a challenge. This approach provides a viable solution to the problem. Children of all ages can be fitted with the minimal invasive portable gait analyzer and left unattended to pursue any activity. After a period of time, data will be retrieved. A portion of normal gait of just a few steps can then be selected and used for data analysis. Example of five normal steps measured on a two year old toddler is shown in FIG. 32. It depicts all essential gait features in details, a feat that is otherwise impossible in a more formal setting with the traditional gait measurement.

Gait Measurement for Animals

Figure 33:
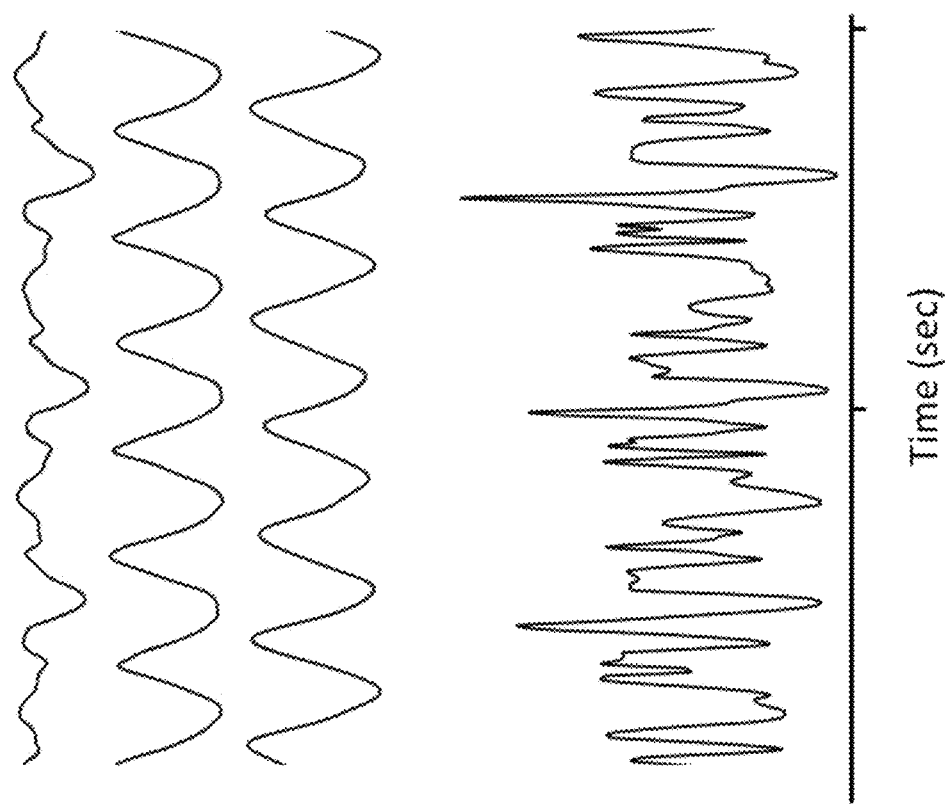
FIG. 33 shows the gait pattern and gait force spectrum of a dog walking.

This method can also be extended to measure the gait of animals due to its simplicity and minimal invasiveness. FIG. 33 gives an example of the gait pattern and the gait force spectrum of a dog walking on at 3 mph. Unlike human being, the dog's gait is most distinctive for its smooth and consistent sinusoidal undulation, but its gait force spectrum is much more complex because the multiple energy injection/rejection channels involving all four limbs.

Case 3—Assessment of the Effectiveness of Therapeutic Treatment

Figure 34:
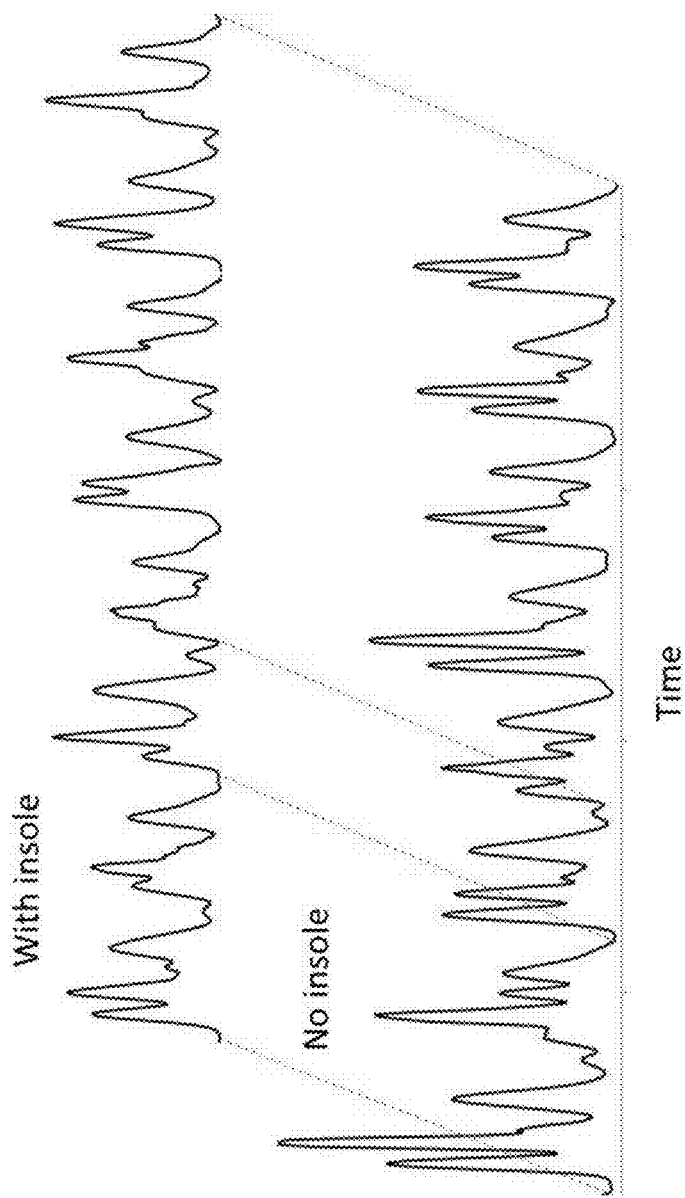
FIG. 34 shows the gait pattern and gait force spectrum of an individual with and without wear customized corrective footwear.

This invention has both research and clinical applications. Aside from providing diagnostic information, it is also useful in assessing the effectiveness of therapeutic treatment including physical rehabilitation and the fitting with corrective measures such as special footwear, and even prostheses. Traditionally, their effectiveness is assessed based on doctor-patient communication, experience of the medical personnel and certain test. This invention provides another option which is simple, with fast turn-around time and minimal invasiveness, while providing in depth and quantitative analysis based on bio-mechanics. FIG. 34 gives an example of the gait pattern of an individual with and without wearing a pair of customize insoles. The less jaggedness and more defined peaks in the gait force spectrum with corrective footwear is a clear indication of the effectiveness. It demonstrate the value of this invention in providing quantitative and scientific based assessment to aid therapeutic decision and be used as a record for tracking long term progress.

Another effective way to access gait quality and its dependence on various corrective measure is by measuring the gait energy partitioned among three components in sway, heave and surge. The magnitude of the fraction of total gait energy partitioned into each component is obtained by the algorithm described above. Each gait measurement is represented as a single data point in the 3-D space with component gait energy fraction as the coordinate axes. This point is known as Gait Energy Partition Index (GEPI). Its location is a measure of stability, forward movement power and coordination. As the gait varies due to different therapeutic measures or footwear design, the GEPI will trend through the 3D space. Its position can be used as a quantitative indicator to assess the effectiveness of the therapeutic measures or the comfort of footwear design so the best solution can be decided.

INDUSTRIAL APPLICABILITY

The present invention relates to a method of gait measurement using tri-axial accelerometer/gyro in mobile devices. In particular, the present invention relates to algorithms for gait measurement using tri-axial accelerometer/gyro in mobile devices for monitoring and improving the physical movement of a moving subject.

If desired, the different functions discussed herein may be performed in a different order and/or concurrently with each other. Furthermore, if desired, one or more of the above-described functions may be optional or may be combined.

While the foregoing invention has been described with respect to various embodiments and examples, it is understood that other embodiments are within the scope of the present invention as expressed in the following claims and their equivalents. Moreover, the above specific examples are to be construed as merely illustrative, and not limitative of the reminder of the disclosure in any way whatsoever. Without further elaboration, it is believed that one skilled in the art can, based on the description herein, utilize the present invention to its fullest extent. All publications recited herein are hereby incorporated by reference in their entirety.

What is claimed is:

1. A method for characterizing movements of a subject using a gait pattern, the method comprising:
    locating a center of gravity of said subject for placement of a mobile device having a tri-axial accelerometer;
    measuring using the tri-axial accelerometer at a predetermined data sampling rate, acceleration data in x, y, and z directions of the center of gravity of said subject;
    identifying a gait cycle from the measured acceleration data, which comprises:
        identifying a time of a heel strike which corresponds to a maximum downward velocity of the center of gravity by performing a integration on the vertical-direction acceleration data, and
        identifying a time of a toe-off which corresponds to a minimum height of the center of gravity by performing a double integration on the vertical-direction acceleration data;
        wherein the gait cycle comprising at least one stride or at least two steps of said subject, and
        wherein said at least one stride or at least two steps comprise at least one heel strike followed by at least one stance phase and at least one swing phase;
    time-marking, based on the measured acceleration data, two or more key events in the gait cycle, the key events comprising the at least one heel strike and at least one mid-single leg support;
    converting the measured acceleration data in all directions to a time dependent power spectrum, which comprises computing a Dynamic Instability Index (DII) at each time-marked event in the gait cycle and constructing time variations of DII to generate the time dependent power spectrum;
    extracting from the measured acceleration data a phase relationship between accelerations along different orientations at each time-marked event in the gait cycle; and
    generating a graphical representation on the phase relationships between accelerations along different orientations;
    wherein the gait pattern of said subject comprises the time dependent power spectrum and the graphical representation of the phase relationships between accelerations along different orientations.

2. The method according to claim 1 wherein the at least one stance phase describes at least one sequence when at least one landing limb of said subject remains on a surface and pushes backwards against said surface until at least one toe-push starts the at least one swing phase.

3. The method according to claim 1 wherein said acceleration data further comprise magnitude, timing, duration and direction of energy flow of said acceleration data.

4. The method according to claim 1 wherein said time dependent power spectrum is expressed either in high time resolution determined by the acceleration data rate or by averaging over a preset interval.

5. The method according to claim 1 wherein said at least one phase relationship between accelerations along different orientations comprises the phase relationship between surge (forward) and heave (vertical) acceleration orientations.

6. The method according to claim 1 wherein said method has uses comprising characterizing normal gaits and abnormal gaits, the abnormal gaits further comprising Leg Length Discrepancy Syndrome, knee tremors, high knee lift, and gaits from hip replacement patients and Parkinson disease patients.

7. The method according to claim 1 wherein said subject are human.

8. The method according to claim 1 wherein said subject are juveniles.

9. An apparatus for characterizing movements of a subject using a gait pattern, comprising:
    a mobile device having a tri-axial accelerometer located approximately at a center of gravity of said subject and configured to measure using the tri-axial accelerometer at a predetermined data sampling rate, acceleration data in x, y, and z directions of the center of gravity of said subject; and
    one or more processors configured to:
        receive the measured acceleration data;
        identify a gait cycle from the measured acceleration data, which comprises:
            identifying a time of a heel strike which corresponds to a maximum downward velocity of the center of gravity by performing a integration on the vertical-direction acceleration data, and
            identifying a time of a toe-off which corresponds to a minimum height of the center of gravity by performing a double integration on the vertical-direction acceleration data;
            wherein the gait cycle comprising at least one stride or at least two steps of said subject, and
            wherein said at least one stride or at least two steps comprise at least one heel strike followed by at least one stance phase and at least one swing phase;
        time-mark, based on the measured acceleration data, two or more key events in the gait cycle, the key events comprising the at least one heel strike and at least one mid-single leg support;
        convert the measured acceleration data to a time dependent power spectrum, the conversion comprising computing a Dynamic Instability Index (DII) at each time-marked event in the gait cycle and constructing tine variations of DII to generate the time dependent power spectrum;
        extract from the measured acceleration data a phase relationship between accelerations along different orientations at each time-marked event in the gait cycle; and
        generate a graphical representation on the phase relationships between accelerations along different orientations;
        wherein the gait pattern of said subject comprises the time dependent power spectrum and the graphical representation of the phase relationships between accelerations along different orientations.

10. The apparatus according to claim 9 wherein the at least one stance phase describes at least one sequence when at least one landing limb of said subject remains on a surface and pushes backwards against said surface until at least one toe-push starts the at least one swing phase.

11. The apparatus according to claim 9 wherein said acceleration data comprise magnitude, timing, duration and direction of energy flow of said acceleration data.

12. The apparatus according to claim 9 wherein said time dependent power spectrum is expressed either in high time resolution determined by the acceleration data rate or by averaging over a preset interval.

13. The apparatus according to claim 9 wherein said at least one phase relationship between accelerations along different orientations comprises the phase relationship between surge (forward) and heave (vertical) acceleration orientations.

14. The apparatus according to claim 9 wherein said apparatus has uses comprising characterizing normal gaits and abnormal gaits, the abnormal gaits further comprising Leg Length Discrepancy Syndrome, knee tremors, high knee lift, and gaits from hip replacement patients and Parkinson disease patients.

15. The apparatus according to claim 9 wherein said subject are human.

16. The apparatus according to claim 9 wherein said subject are juveniles.

\* \* \* \* \*